US006838084B1

(12) United States Patent
Jochmus et al.

(10) Patent No.: US 6,838,084 B1
(45) Date of Patent: Jan. 4, 2005

(54) CYTOTOXIC T-CELL EPITOPES OF THE PAPILLOMA VIRUS L1-PROTEIN AND USE THEREOF IN DIAGNOSIS AND THERAPY

(75) Inventors: Ingrid Jochmus, Gröbenzell (DE); John Nieland, München (DE)

(73) Assignee: MediGene Aktiengesellschaft, Martinsried (DE)

( * ) Notice: Subject to any disclaimer, the term of this patent is extended or adjusted under 35 U.S.C. 154(b) by 0 days.

(21) Appl. No.: 09/980,177

(22) PCT Filed: May 31, 2000

(86) PCT No.: PCT/EP00/05006

§ 371 (c)(1),
(2), (4) Date: May 2, 2002

(87) PCT Pub. No.: WO00/73335

PCT Pub. Date: Dec. 7, 2000

(30) Foreign Application Priority Data

Jun. 1, 1999 (DE) ........................................ 199 25 199

(51) Int. Cl.[7] .............................................. A61K 39/12
(52) U.S. Cl. .................. 424/204.1; 530/300; 536/23.72
(58) Field of Search ........................... 424/204.1, 186.1; 435/343.2; 530/30; 536/23.72

(56) References Cited

U.S. PATENT DOCUMENTS

| 4,777,239 | A | | 10/1988 | Schoolnik et al. |
|---|---|---|---|---|
| 5,415,995 | A | | 5/1995 | Schoolnik et al. |
| 5,547,846 | A | | 8/1996 | Bartsch et al. |
| 5,629,146 | A | * | 5/1997 | Dillner et al. ................. 435/5 |
| 5,629,161 | A | | 5/1997 | Müller et al. |
| 5,662,907 | A | | 9/1997 | Kubo et al. |
| 5,747,269 | A | | 5/1998 | Rammensee et al. |
| 6,025,163 | A | | 2/2000 | Shamanin et al. |
| 6,183,746 | B1 | | 2/2001 | Urban et al. |

FOREIGN PATENT DOCUMENTS

| CA | 2140591 | | 7/1995 |
|---|---|---|---|
| EP | 0 375 555 | | 6/1990 |
| EP | 0 386 734 | | 9/1990 |
| EP | 0 451 550 A2 | | 10/1991 |
| GB | 2 279 651 | | 6/1994 |
| WO | WO 90/04790 | * | 5/1990 |
| WO | WO 91/18294 | | 11/1991 |
| WO | WO 92/05248 | | 4/1992 |
| WO | WO 92/10513 | | 6/1992 |
| WO | WO 93/02184 | | 2/1993 |
| WO | WO 93/20844 | | 10/1993 |
| WO | WO 93/22338 | | 11/1993 |
| WO | WO 94/05792 | | 3/1994 |
| WO | WO 94/20137 | | 9/1994 |
| WO | WO 95/01374 | | 1/1995 |
| WO | WO 96/11272 | | 4/1996 |
| WO | WO 96/33737 | | 10/1996 |
| WO | WO 98/05790 | | 2/1998 |
| WO | WO 98/23752 | | 6/1998 |
| WO | WO 99/03885 | | 1/1999 |
| WO | WO 99/18220 | | 4/1999 |
| WO | WO 99/65522 | | 12/1999 |

OTHER PUBLICATIONS

Chan et al, Journal of Virology, Oct. 1992, vol. 66, No. 10, pp. 5714–5725.*
Altman et al., "Phenotypic Analysis of Antigen–Specific T Lymphocytes," *Science* 274:94–96 (1996).
Baker et al., "Structures of Bovine and Human Papillomaviruses," *Biophys. J.* 60:1445–1456 (1991).
De Bruijn et al., "Mechanisms of Induction of Primary Virus–Specific Cytotoxic T Lymphocyte Responses," *Eur. J. Immunol.* 22:3013–3020 (1992).
De Bruijn et al., "Peptide Loading of Empty Major Histocompatibility Complex Molecules on RMA–S Cells Allows the Induction of Primary Cytotoxic T Lymphocyte Responses," *Eur. J. Immunol.* 21:2963–2970 (1991).
De Gruijl et al., "Immune Responses Against Human Papillomavirus (HPV) Type 16 Virus–Like Particles in a Cohort Study of Women with Cervical Intraepithelial Neoplasia 1. Differential T–Helper and IgG Responses in Relation to HPV Infection and Disease Outcome," *Journal of General Virology* 80:399–408 (1999).
Dunbar et al., "Direct isolation, Phenotyping and Cloning of Low–Frequency Antigen–Specific Cytotoxic T Lymphocytes From Peripheral Blood," *Current Biology* 8:413–416 (1998).
Feltkamp et al., "Vaccination with a Cytotoxic T Lymphocyte–Containing Peptide Protects Against a Tumor Induced by Human Papillomavirus Type 16–Transformed Cells," *Eur. J. Immunol.* 23:2242.2249 (1993).
Gossen et al., "Inducible Gene Expression Systems for High Eukaryotic Cells," *Current Opinion in Biotechnology* 5:516–520 (1994).
Heino et al., "Human Papillomavirus Type 16 Capsids Expose Multiple Type–Restricted and Type–Common Antigenic Epitopes," *Journal of General Virology* 76:1141–1153 (1995).
Kast et al., "Role of HLA–A Motifs in Identification of Potential CTL Epitopes in Human Papillomavirus Type 16 E6 and E7 Proteins," *Journal of Immunology* 152:3904–3912 (1994).

(List continued on next page.)

Primary Examiner—Ali R. Salimi
(74) Attorney, Agent, or Firm—Clark & Elbing LLP

(57) ABSTRACT

The present invention relates to a papillomavirus T-cell epitope having an amino acid sequence ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), SMVTSDAQI (SEQ ID NO: 17), and/or to a functionally active variant thereof, and also to their use in diagnostics and therapy.

1 Claim, 8 Drawing Sheets

OTHER PUBLICATIONS

Figure 1:
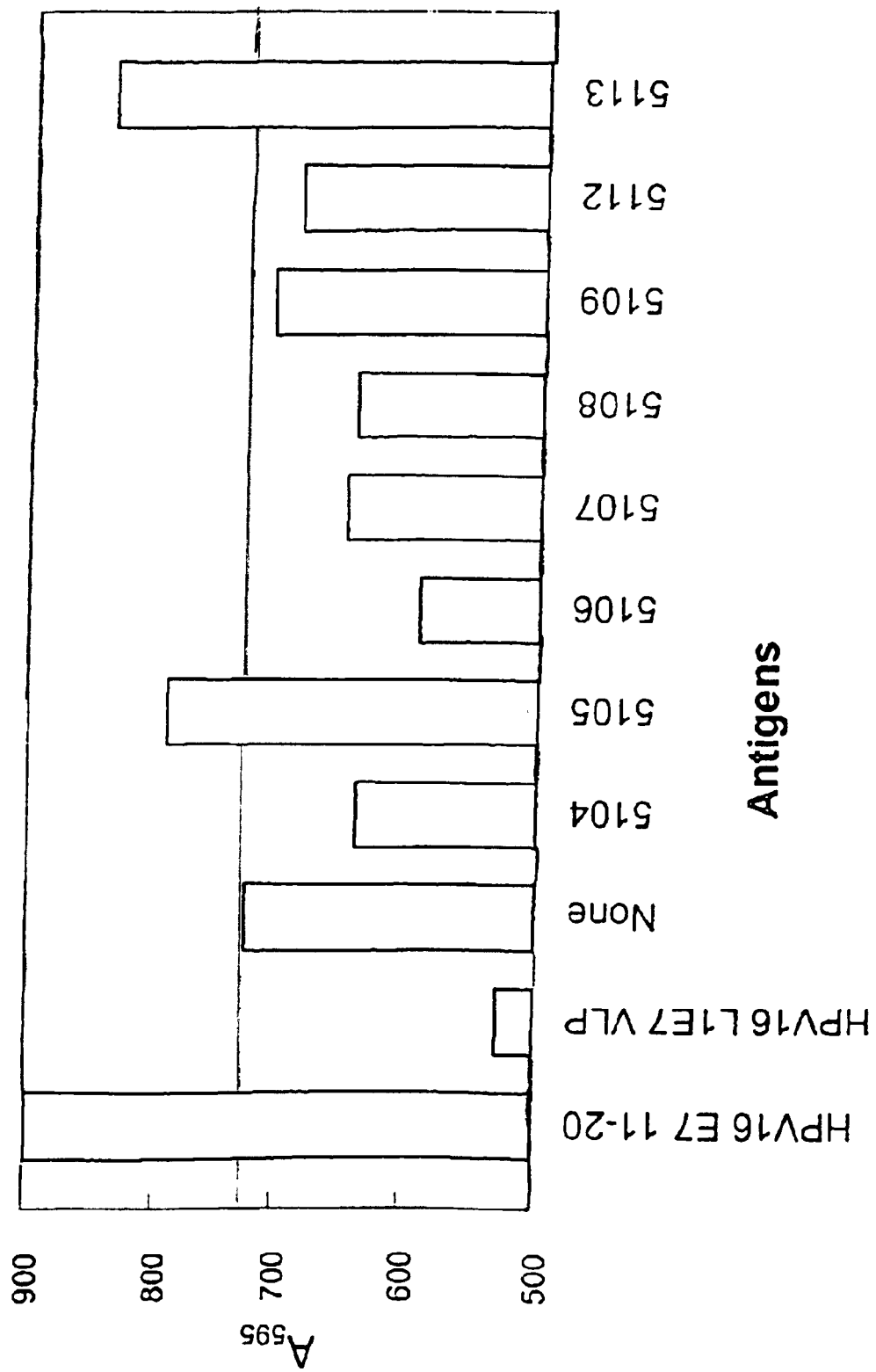

Krchnak et al., "Synthetic Peptides Derived From E7 Region of Human Papillomavirus Type 16 used as Antigens in ELISA," *Journal of General Virology* 71:2719–2724 (1990).

Müller et al., "Identification of Seroreactive Regions of the Human Papillomavirus Type 16 Proteins E4, E6, E7, and L1," *Journal of General Virology* 71:2709–2717 (1990).

Müller et al., "Chimeric Papillomavirus–Like Particles," *Virology* 234:94–111 (1997).

Nieland et al., "Chimeric Papillomavirus Virus–Like Particles Induce a Murine Self–Antigen–Specific Protective and Therapeutic Antitumor Immune Response," *Journal of Cellular Biochemistry* 71:145–152 (1999).

Parker et al., "Scheme for Ranking Potential HLA–A2 Binding Peptides Based on Independent Binding of Individual Peptide Side–Chains," *Journal of Immunology* 152:163–175 (1994).

Peng et al., "Papillomavirus Virus–Like Particles Can Deliver Defined CTL Epitopes to the MHC Class 1 Pathway," *Virology* 240:147–157 (1998).

Rudolf et al, "Induction of HPV16 Capsid Protein–Specific Human T Cell Responses by Virus–Like Particles," *Biol. Chem.* 380:335–340 (1999).

Schäfer et al., "Immune Response to Human Papillomavirus 16 L1E7 Chimeric Virus–Like Particles: Induction of Cytotoxic T Cells and Specific Tumor Protection," *Int. J. Cancer* 81:881–888(1999).

Sijts et al., "Cytotoxic T Lymphocytes Against the Antigen–Processing–Defective RMA–S Tumor Cell Line," *Eur. J. Immunol.* 22:1639–1642 (1992).

Sijts et al., "Immunodominant Mink Cell Focus–Inducing Murine Leukemia Virus (MuLV)–Encoded CTL Epitope, Identified by Its MHC Class I–Binding Motif, Explains MuLV–Type Specificity of MCF–Directed Cytotoxic T Lymphocytes," *Journal of Immunology* 152:106–116 (1994).

Tsukui et al., "Interleukin 2 Production in Vitro by Peripheral Lymphocytes in Response to Human Papillomavirus–Derived Peptides: Correlation with Cervical Pathology," *Cancer Research* 56:3967–3974 (1996).

Zhou et al, "Definition of Linear Antigenic Regions of the HPV 16 L1 Capsid Protein Using Synthetic Virion–Like Particles," *Virology* 189:592–599 (1992).

Zwicker et al., "Cell–Cycle Regulation of Gene Expression by Transcriptional Repression," *TIG* 13:3–6 (1997).

\* cited by examiner

CYTOTOXIC T-CELL EPITOPES OF THE PAPILLOMA VIRUS L1-PROTEIN AND USE THEREOF IN DIAGNOSIS AND THERAPY

This application is the U.S. National Stage of International Application No. PCT/EP2000/05006, filed May 31, 2000, which claims the benefit of German Application No. 19925199.1, filed Jun. 1, 1999.

The present invention related to a papillomavirus T-cell epitope having an amino acid sequence ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNY-FPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), SMVTSDAQI (SEQ ID NO: 17), and/or to a functionally active variant thereof, and also to its use in diagnostics and therapy.

The papillomaviruses, also called wart viruses, are double-stranded DNA viruses with a genome size of about 8000 base pairs and an icosahedral capsid of approx. 55 nm in diameter. Up until now, more than 100 different human-pathogenic papillomavirus types (HPV) are known, some of which, for example HPV-16, HPV-18, HPV-31, HPV-33, HPV-39, HPV-45, HPV-52 or HPV-58, may cause malignant tumors and others, for example HPV-6, HPV-11 or HPV-42, may cause benign tumors.

The papillomavirus genome can be divided into three parts: the first part relates to a noncoding region containing regulatory elements for virus transcription and replication. The second region, the "E" (early) region, contains various protein-encoding sections E1–E7 of which, for example, the E6 and E7 proteins are responsible for transformation of epithelial cells and the E1 protein controls the DNA copy number. The E6 and E7 regions are "oncogenes" which are also expressed in malignantly degenerate cells. The third region, also called L (late) region, contains two protein-encoding sections L1 and L2 which code for structural components of the virus capsid. Over 90% of the L protein is present in the viral capsid, the L1:L2 ratio generally being 30:1. In accordance with the present invention, the term L1 protein means the main capsid protein of papillomaviruses (Baker T. et al. (1991) Biophys. J. 60, 1445).

In over 50% of cases, HPV-16 is connected with cervical cancer (carcinoma of the cervix). HPV-16 is the main risk factor for the formation of cervical neoplasms. The immune system plays an important part in the progress of the disease. Thus, cellular immune responses and in particular antigen-specific T lymphocytes are presumably important for the defense mechanism. It has furthermore been found that in high-grade malignant cervical intraepithelial neoplasms (CIN II/III) and cervical tumors the E7 gene is expressed constitutively in all layers of the infected epithelium. The E7 protein in particular is therefore considered as a potential tumor antigen and as a target molecule for activated T cells (see, for example, WO 93/20844). The E7-induced cellular immune response in the patient, however, is apparently not strong enough to influence the course of the disease. The immune response may possibly be amplified by suitable vaccines.

It has been possible to show that expression of the L1 gene and/or coexpression of the L1 and L2 genes can lead to the formation of capsomers, stable capsomers, capsids or virus-like particles (VLPs) (see, for example, WO 93/02184, WO 94/20137 or WO 94/05792). Capsomers mean an oligomeric configuration which is composed of five L1 proteins. The capsomer is the basic building block of which viral capsids are composed. Stable capsomers mean capsomers which are incapable of assembling to form capsids. Capsids mean the papillomavirus coat which is, for example, composed of 72 capsomers (Baker T. et al. (1991) Biophys. J. 60, 1445). VLP means a capsid which is morphologically and in its antigenicity identical to an intact virus. It was possible to use the VLPs in various animal systems for causing a humoral immune response characterized by the formation of neutralizing antibodies. The formation of virus-neutralizing antibodies against L1 and/or L2 protein, however, is of relatively low clinical importance if the virus infection has already taken place, since for the elimination of virus-infected cells a virus-specific cytotoxic T-cell (CTL) response rather than antibodies seems to be necessary. And, although VLPs are capable of causing a cytotoxic T-cell response, an immune response exclusively directed against the capsid proteins L1 and/or L2 appears unsuitable for controlling a tumor caused by papillomaviruses.

Therefore, "chimeric papillomavirus-like particles" (CVLPs) which comprise a fusion protein of the capsid protein L1 and the potential tumor antigen E7 (WO 96/11272 and Müller, M. et al. (1997) Virology, 234, 93) have been developed. The CVLPs caused only to a small extent a humoral immune response directed against the E7 protein (Müller, M. et al. (1997), supra). Some of the CVLPs tested, however, do indeed induce the desired E7-specific cytotoxic T-cell response in mice (see also Peng S. et al. (1998) Virology 240, 147–57). Therefore, CVLPs are of interest both for the development of a vaccine and for the treatment of already established infections and tumors resulting therefrom, since the E7 tumor cell peptides presented via MHC molecules of class I would represent target molecules of cytotoxic T cells.

A vaccine comprising CVLPs is based on the principle of the CVLPs pseudo-infecting cells. This means that CVLPs and viruses alike get into the cell, are processed there to peptides, and the peptides are then loaded onto MHC class I and II molecules and finally presented to CD8- or CD4-positive T cells. As a consequence of this stimulation, CD8 cells may differentiate into cytotoxic T cells and then cause a cellular immune response, whereas CD4 cells develop into T helper cells and stimulate B cells to give a humoral or CD8-positive T cells to give a cytotoxic immune response and may themselves induce lysis of infected cells.

Small peptides may bind to MHC class I molecules already on the cell surface and then stimulate without further processing CD8- or CD4-positive cells to give a cellular immune response. However, a particular peptide can be bound only by particular MHC molecules. Due to the large polymorphism of MHC molecules in natural populations, a particular peptide can therefore be bound and presented only by a small part of a population. In accordance with the present invention, presentation means binding of a peptide or protein fragment to an MHC molecule, it being possible for said binding to take place, for example, in the endoplasmic reticulum, the extracellular space, the endosomes, proendosomes, lysosomes or protysosomes, and said MHC molecule-peptide complex then being bound on the extracellular side of the cell membrane so that it can be recognized specifically by immune cells.

Since CVLPs cause both a cellular and a humoral immune response and are not MHC-restricted, this technology is generally suitable for the development of vaccines, since an L1 portion provides the ability to form particles and an additional antigen portion is fused to said L1 portion.

For the development of CVLPs of this kind it is absolutely necessary to have a functional assay system available which can be used to study directly the immunogenicity of CVLPs. Such an assay system should have the property that CVLPs with different antigen proportions can be studied by using the same assay system. Since the cellular immune response is of crucial importance for immunological therapies of tumors or viral diseases, the object arose to make it possible to measure the cellular immune response caused by CVLPs.

This object was achieved by identifying T-cell epitopes which in connection with the MHC molecules, and in a particular embodiment with HLA A2.01 MHC molecules, cause, for example, a cytotoxic T-cell response in vivo and in vitro. Said peptides preferably have the sequence ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), SMVTSDAQI (SEQ ID NO: 17). These sequences are part of the L1 and E7 peptides of HPV16. They include the amino acid regions L1 86–94 (5104), L1 123–131 (5106), L1 285–293 (5107), L1 275–283 (5108), L1 238–246 (5109), L1 426–434 (5112), L1 28–39 (2016), L1 311–320 (2017), L1 408–417 (2018), L1 38–47 (2019), L1 396–404 (2020), L1 349–357 (2022), L1 298–306 (27/28), L1 90–98 (9), E7 1–9 (43), E7 18–25 (45) and E7 44–53 (47/48). The names of the relevant epitopes is indicated in brackets.

The E7 peptides 43, 45 and 47/48 have already been published as potential epitopes in Kast et al., (1994) Journal of Immunology 152, 3904–3912. However, this publication only shows that said peptides can bind to HLA A1 molecules, but does not show that a cytotoxic T-cell response can actually be caused. Furthermore, no data are given which prove that T cells recognize the peptides as part of a protein. For it has been shown many times that peptides binding per se to HLA molecules are not necessarily also recognized by T cells. Moreover, it is known that T cells, although recognizing a peptide, which recognition can be measured by the ability of a peptide to induce a T-cell response in said cells, do not necessarily also recognize cells which have been loaded with whole proteins containing the corresponding peptide. This can be explained by the fact that peptides often contain protease cleavage sites within which the peptides, during processing of the whole proteins in the cell, are cut and thus destroyed and thus cannot be detected any longer by T cells. This problem is confirmed, for example, in Feltkamp et al. (1993), Eur. J. Immunol. 23: 2242–2249.

The present invention therefore relates to a T-cell epitope having an amino acid sequence ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), SMVTSDAQI (SEQ ID NO: 17), and/or to a functionally active variant thereof.

A functionally active variant of ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16) or SMVTSDAQI (SEQ ID NO: 17) means a T-cell epitope which, in a T-cell cytotoxicity assay system (see, for example, Examples 2–5 of the present invention), has a cytotoxicity which, compared to the cytotoxicity of ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16) or SMVTSDAQI (SEQ ID NO: 17), corresponds to at least the sum of the average of the negative controls and three times the standard deviation, preferably of at least approx. 30%, in particular at least approx. 50% and particularly preferably of at least approx. 80%.

An example of a preferred variant is a T-cell epitope having a sequence homology to ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), or SMVTSDAQI (SEQ ID NO: 17) of at least approx. 65% preferably at least approx. 75% and in particular at least approx. 85% at the amino acid level. Other preferred variants are also T-cell epitopes which are structurally homologous to ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), or SMVTSDAQI (SEQ ID NO: 17). Such epitopes may be found by generating specific T cells against the T-cell epitopes ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), ICWGNQLFV (SEQ ID NO: 12), FYNPDTQRL (SEQ ID NO: 13), MHGDTPTLH (SEQ ID NO: 14), ETTDLYCY (SEQ ID NO: 15), QAEPDRAHYN (SEQ ID NO: 16), or SMVTSDAQI (SEQ ID NO: 17) (DeBruijn M. L. et al (1991) Eur. J. Immunol. 21, 2963–70; and DeBruijn M. L. (1992) Eur. J. Immunol. 22, 3013–20) and assaying, for example, synthetically produced peptides of choice for recognition by the peptide-specific T cells (see examples). The T-cell epitopes in particular mean cytotoxic T-cell epitopes. However, noncytotoxic T cells are also known which can likewise recognize MHC I molecules so that the present invention also includes noncytotoxic T-cell epitopes as variant.

Another embodiment of the present invention is a T-cell. epitope which is part of a compound, the compound not being a naturally occurring L1 protein of a papillomavirus and not being an exclusively N-terminal or exclusively C-terminal deletion mutant of a naturally occurring L1 protein of a papillomavirus.

In a particular embodiment, a T-cell epitope having an amino acid sequence ILVPKVSGL (SEQ ID NO: 1), RLVWACVGV (SEQ ID NO: 2), HLFNRAGTV (SEQ ID NO: 3), YLRREQMFV (SEQ ID NO: 4), TLQANKSEV (SEQ ID NO: 5), ILEDWNFGL (SEQ ID NO: 6), SLWLPSEATVYL (SEQ ID NO: 7), NLASSNYFPT (SEQ ID NO: 8), TLTADVMTYI (SEQ ID NO: 9), YLPPVPSKV (SEQ ID NO: 10), YDLQFIFQL (SEQ ID NO: 11), ICWGNQLFV (SEQ ID NO: 12), and/or a functionally active variant may be contained in an L1 protein of a different papillomavirus or in a chimeric L1 protein, for example an HPV18L1E7 fusion protein. Such a compound of the invention may have the ability to form CVLPs.

As part of a compound, said T-cell epitope may preferably be a polypeptide which preferably contains further amino acid sequences, and in particular a fusion protein. In particular, the compound may be a polypeptide of at least approx. 50 amino acids, preferably of at least approx. 35 amino acids, in particular of at least approx. 20 amino acids and particularly preferably of at least approx. 9–12 amino acids, in length.

In order to detect the compound or to modify its T-cell binding activity, said compound may contain a chemical, radioactive isotope, nonradioactive isotope and/or fluorescent label of the T-cell epitope and/or of said fusion protein.

Examples of chemical substances known to the skilled worker, which are suitable for chemical labeling according to the invention, are: biotin, FITC (fluorescein isothiocyanate) or streptavidin.

In a possible embodiment a peptide is modified such that it contains at least one lysine. In a manner known to the skilled worker biotin or FITC (fluorescein isothiocyanate) is coupled to said lysine. A peptide modified in this way is bound to an appropriate MHC molecule or to a cell containing appropriate MHC molecules. The peptide may then be detected via labeled avidin or streptavidin or directly via FITC fluorescence.

Examples of isotopes known to the skilled worker, which are suitable for radioactive isotope labeling according to the invention are: $^3$H, $^{125}$I, $^{131}$I $^{32}$P, $^{33}$P or $^{14}$C.

Examples of isotopes known to the skilled worker, which are suitable for nonradioactive isotope labeling according to the invention are: $^2$H, or $^{13}$C.

Examples of fluorescent substances known to the skilled worker, which are suitable for fluorescence labeling according to the invention are: $^{152}$Eu, fluorescein isothiocyanate, rhodamine, phycoerythrin, phycocyanin, allophycocyanin, o-phtaldehyde or fluorescamine.

Further label not listed here, which may also be used for labeling in accordance with this invention, are known to the skilled worker.

Examples of inventive chemical modifications known to the skilled worker are the transfer of acetyl, phosphate and/or monosaccharide groups.

Inventive polypeptides of approx. 50 amino acids in length may be prepared, for example, by chemical peptide synthesis. Longer polypeptides are preferably generated by genetic engineering. The present invention therefore further relates to a nucleic acid construct for expressing said T-cell epitope or compounds containing the following components: (a) at least one regulatory element and (b) at least one nucleic acid coding for an amino acid sequence of the compound of the invention. Said nucleic acid construct is preferably made of DNA or RNA. Suitable regulatory elements allow, for example, constitutive, regulatable, tissue-specific, cell cycle-specific or metabolically specific expression in eukaryotic cells or constitutive, metabolically specific or regulatable expression in prokaryotic cells. Regulatable elements according to the present invention are promoters, activator sequences, enhancers, silencers, and/or repressor sequences.

Examples of suitable regulatable elements which make constitutive expression in eukaryotes possible are promoters recognized by RNA polymerase III or viral promoters such as CMV enhancer, CMV promoter, SV40 promoter and viral promoter and activator sequences derived, for example, from HBV, HCV, HSV, HPV, EBV, HTLV or HIV.

Examples of regulatable elements which make regulatable expression in eukaryotes possible are the tetracyclin operator in combination with a corresponding repressor (Gossen M. et al (1994) Curr. Opin. Biotechnol. 5, 516–20).

Examples of regulatable elements which make tissue-specific expression in eukaryotes possible are promoters or activator sequences from promoters or enhancers of those genes coding for proteins which are expressed only in particular cell types.

Examples of regulatable elements which make cell cycle-specific expression in eukaryotes possible are the promoters of the following genes: cdc25C, cyclin A, cyclin E, cdc2, E2F, B-myb or DHFR (Zwicker J. and Müller R. (1997) Trends Genet. 13, 3–6).

Examples of regulatable elements which make metabolically specific expression in eukaryotes possible are promoters regulated by hypoxia, by glucose deficiency, by phosphate concentration or by heat shock.

In order to make it possible to introduce said nucleic acid and thus express the polypeptide in a eukaryotic or prokaryotic cell by transfection, transformation or infection, the nucleic acid may be present as plasmid, or as part of a viral or nonviral vector. The present invention therefore further relates to a vector, in particular an expression vector which contains a nucleic acid coding for a polypeptide of the invention. Viral vectors particularly suitable here are: baculo viruses, vaccinia viruses, adenoviruses, adeno associated viruses and herpes viruses. Nonviral vectors particularly suitable here are: virosomes, liposomes, cationic lipids or polylysine-conjugated DNA.

The present invention further relates to a cell containing, preferably presenting, at least one T-cell epitope. In a particular embodiment, the cell is transfected, transformed or infected by one of the vectors mentioned. This cell expresses the polypeptide of the invention under conditions known to a skilled worker which lead to activation of the regulatable elements used in each case. The polypeptide can then be isolated from said cell and purified, for example by using one of the abovementioned labels. Cells which are suitable for the preparation by genetic engineering and subsequent purification of the expressed compounds of the invention are prokaryotic and eukaryotic cells, in particular bacteria cells such as, for example, *E.coli*, yeast cells such as, for example, *S. cerevisiae*, insect cells such as, for example, *Spodoptera frugiperda* cells (Sf-9) or *Trichoplusia ni* cells or mammalian cells such as, for example, COS cells or HeLa cells.

A particular embodiment is using the cell itself which expresses the polypeptide of the invention, and, in a particularly preferred embodiment, the cell presents parts of the polypeptide of the invention via MHC-1 molecules on the cell surface. Suitable cells for preparing the cell of the invention are antigen-presenting cells such as, for example, B cells, macrophages, dendritic cells, fibroblasts or other HLA A2.01-positive cells, in a preferred embodiment JY, T2, CaSki cells or EBV-transformed B-cell lines. The cells of the invention which present a polypeptide containing a T-cell epitope may be employed as target cells for restimulating immune cells, in particular T cells, and/or for measuring T-cell activation. A target cell means in accordance with the present invention a cell which presents a T-cell epitope via MHC molecules and thus specifically causes T-cell activation, in particular a cytotoxic T-cell reaction against the cell.

Furthermore, the T-cell epitope-containing compound may be part of a complex which is characterized by the compound being linked covalently or by hydrophobic interactions, ionic binding or hydrogen bonds to at least one further species such as peptides, proteins, peptoids, linear or branched oligo or polysaccharides and nucleic acids.

The present invention therefore relates to a complex containing a T-cell epitope or a compound and at least one further compound. In a preferred embodiment, the polypeptide is linked to MHC class I molecules, preferably as HLA A2.01 tetramer. Particular preference is given to human MHC class I molecules. Using the technique by Altman J. D. et al. (1996, Science 274, 94–6) it is possible, for example, to prepare HLA A2.01 tetramers with the appropriate bound peptides which are capable of binding to T-cell receptors of peptide-specific cytotoxic T cells.

Another embodiment is immobilization of the compound of the invention or of said complex to support materials. Examples of suitable support materials are ceramic, metal, in particular noble metal, glasses, plastics, crystalline materials or thin layers of this support, in particular of said materials, or (bio)molecular filaments such as cellulose or structural proteins.

In order to purify the complex of the invention, a component of the complex may additionally also contain a protein tag. Protein tags of the invention allow, for example, high-affinity absorption to a matrix, stringent washing with suitable buffers with negligible elution of the complex and subsequent specific elution of the absorbed complex. Examples of protein tags known to the skilled worker are an $(HIS)_6$ tag, a myc tag, a FLAG tag, a hemagglutinin tag, glutathione transferase (GST) tag, intein with chitin-binding affinity tag or maltose-binding protein (MBP) tag. The protein tags of the invention may be located N-terminally, C-terminally and/or internally.

The present invention also relates to a method for in vitro detection of the activation of T cells by at least one compound containing a T-cell epitope. A method of this kind preferably comprises three steps:

a) In a first step, cells are stimulated by at least one compounds containing a T-cell epitope. This compound may be at least one inventive compound containing a T-cell epitope, at least one inventive complex containing a T-cell epitope, at least one capsomer, at least one stable capsomer, at least one VLP, at least one CVLP, and/or at least one virus. In a preferred embodiment, immune cells are stimulated by incubation with CVLPs. This stimulation may be carried out, for example, in the form of a vaccination or by incubating immune cells with CVLPs in vitro. Immune cells stimulated in this way are obtained, for example, after a vaccination or, in the case of a tumor patient, from the blood, from tumors or from lymph nodes, and/or are cultured.

b) In a second step, the cells are incubated with at least one T-cell epitope of the invention, at least one inventive compound containing a T-cell epitope, at least one target cell presenting a T-cell epitope and/or with at least one complex of the invention.

c) In a third step, T-cell activation is determined. Examples of methods suitable for this are detection of cytokine production or secretion by the T cells, of the surface molecule expression on T cells, of target cell lysis or of cell proliferation. Examples of methods suitable for this are a cytokinassay (Chapter 6.2 to 6.24 in Current Protocols in Immunology (1999), edited by Coligan J. E., Kruisbeek A. M., Margulies D. H., Shevach E. M. and Strober W., John Wiley & Sons), ELISPOT (Chapter 6.19 in Current Protocols in Immunology, supra), a $^{51}Cr$ release assay (Chapter 3.11 in Current Protocols in Immunology, supra) or detection of proliferation (Chapter 3.12 in Current Protocols in Immunology, supra). Depending on the method used, it is in this connection also possible to distinguish between the immune cells such as cytotoxic T cells, T helper cells, B cells, NK cells, and other cells. The use of inventive compounds, complexes, and/or cells containing the labels of the invention allows detection of T cells recognizing the T-cell epitope via detection of the binding of labeled compounds, complexes and/or cells to the T cells. In a preferred embodiment, binding of inventive MHC-polypeptide complexes to the surface of T cells is detected. This may be carried out such that the MHC complexes are labeled themselves, for example fluorescently labeled, or that, in a further step, an MHC-specific, labeled, for example fluorescently labeled, antibody is used in order to detect in turn the MHC complexes. The fluorescent label of the T cells can then be measured and evaluated, for example, in a fluorescence-activated cell sorter (FACS). Another possible way of detecting binding of the complexes to the T cells is again measuring T-cell activation (cytokine assay, Elispot, $^{51}Cr$ release assay, proliferation, see above). However, this requires simultaneous stimulation of coreceptors (e.g. CD28), for example by coreceptor-specific antibodies (anti-CD28) and/or other unspecific activators (IL-2).

The present invention also relates to a method containing an additional step a') which is introduced after step a).

a') In this additional step a') which follows step a), the isolated or cultured cells are cocultured width at least one target cell loaded with an inventive compound containing a T-cell epitope, at least one inventive complex containing a T-cell epitope, at least one capsomer, at least one stable capsomer, at least one VLP, at least one CVLP and/or at least one virus, with at least one inventive complex containing a T-cell epitope, and/or at least one target cell presenting a T-cell epitope for at least approx. 8 weeks, in particular for at least approx. 1 week, prior to step b).

Coculturing means growing cells:
(i) in the presence of at least one target cell loaded with an inventive compound containing a T-cell epitope, at least one inventive complex containing a T-cell epitope, at least one capsomer, at least one stable capsomer, at least one VLP, at least one CVLP, and/or at least one virus,
(ii) in the presence of at least one inventive complex containing a T-cell epitope,
(iii) in the presence of at least one target cell presenting a T-cell epitope, in the same growth medium and the same tissue culture container.

The present invention further relates to a method for preparing a target cell presenting a T-cell epitope. It is possible here to load the target cell with combinations of different T-cell epitopes. In a preferred embodiment, the target cell is incubated with at least one compound containing a T-cell epitope and/or at least one complex containing a T-cell epitope. In a particularly preferred embodiment, the target cell is incubated in growth medium containing polypeptides of the invention or with MHC class I complexes with bound polypeptides of the invention. The MHC class I complexes may be present for example as HLA A2.01 tetramers. In this connection, a tetramer normally binds four peptides. These can be identical or else represent different peptide species. In a further preferred embodiment, the target cell is transfected, transformed and/or infected with a nucleic acid and/or a vector. In a particularly preferred embodiment, the target cell is infected with a vaccinia virus vector. The method of the invention is carried out using antigen-presenting cells, for example B cells, macrophages, dendritic cells, embryonal cells or fibroblasts or other HLA A2.01-positive cells, and, in a preferred embodiment, using JY, T2, CaSki cells or EBV-transformed B-cell lines.

The CVLPs used contain a papillomavirus L1 protein or variants thereof, in particular HPV16 L1 protein and, but not necessarily, a protein heterologous to an L1 or variants thereof. The two proteins may be bound directly or indirectly. In accordance with the invention, directly bound means that the two proteins are covalently bound to one another, for example via a peptide bond or a disulfide bond. Indirectly bound means that the proteins are bound via noncovalent bonds, for example hydrophobic interactions, ionic bonds or hydrogen bonds. In a further embodiment, the CVLPs contain, in addition to L1 protein or variants thereof, a papillomavirus L2 protein.

Examples of a preferred embodiment of the L1 protein of the present invention are L1 proteins having one or more deletions, in particular a C-terminal deletion. A C-terminal deletion has the advantage that it is possible to increase the efficiency of virus-like particle formation, since the nuclear localization signal located at the C terminus is deleted. The C-terminal deletion is therefore preferably up to approx. 35 amino acids, in particular approx. 25 to approx. 35 amino acids, especially approx. 32 to approx. 34 amino acids. For example, a 32 amino acid long C-terminal deletion of the HPV16 L1 protein is sufficient in order to be able to increase the formation of virus-like particles at least approx. ten times. Furthermore, the L1 protein may carry one or more mutations or the L1 portion may be composed of L1 proteins of various papillomaviruses. A common characteristic of the L1 proteins of the invention is the fact that they permit the formation of VLPs or CVLPs and that they contain at least one T-cell epitope of the invention.

In a preferred embodiment, the L1 protein or variants thereof and the protein heterologous to L1 are a fusion protein. Heterologous proteins which are composed of a plurality of various proteins or parts thereof are also included. These ray also be, for example, epitopes, in particular cytotoxic T-cell epitopes, of proteins. In this connection, epitopes in accordance with the invention may also be part of a synthetic polypeptide of approx. 50 amino acids, preferably of at least approx. 35 amino acids, in particular of at least approx. 20 amino acids and particularly preferably of at least approx. 9 amino acids, in length.

Preference is given to proteins heterologous to L1, which are derived from a viral protein, for example derived from HIV, HBV or HCV, preferably from papillomaviruses, in particular from human papillomaviruses.

In a preferred embodiment, said viral protein is a papillomavirus E protein, preferably an E6 and/or E7 protein. It is particularly preferred if the E protein is a deleted E protein, preferably a C-terminally deleted, in particular a C-terminally deleted E7 protein, since these constructs in connection with deleted L1 protein can form preferably virus-like particles. Particular preference is given to deletions of up to 55 amino acids, preferably approx. 5 to approx. 55 amino acids, in particular approx. 38 to approx. 55 amino acids.

In a further embodiment, the protein heterologous to L1 may originate from antigens of nonviral pathogens. Likewise, they may be derived from autoimmune antigens such as, for example, thyroglobulin, myelin basic protein or zona pellucida glycoprotein 3 ($ZP_3$), which are associated with particular autoimmune diseases such as, for example, thyroiditis, multiple sclerosis, oophoritis or rheumatoid arthritis. In a preferred embodiment, the protein heterologous to L1 originates from tumor antigens, preferably melanoma antigens such as MART, ovarian carcinoma antigens such as Her2 neu (c-erbB2), BCRA-1 or CA125, colon carcinoma antigens such as CA125 or breast carcinoma antigens such as Her2 neu (c-erbB2), BCRA-1, BCRA-2.

The present invention further relates to a method for in vitro detection of the activation of T cells which are obtained by preparation from samples. This method makes it possible to determine if a sample, for example a blood sample of a patient, or tumors or lymph nodes of a tumor patient contain papillomavirus L1-protein-specific cytotoxic T cells. A detection method of this kind comprises the following steps:
a") In a first step, cells are obtained, for example by taking blood from a patient or by preparation, for example, of tumors or lymph nodes. Subsequently, the cells are taken up in growth medium and cultured.
b) In a second step, cells are incubated with at least one target cell presenting a T-cell epitope or with at least one complex which comprises as a component a compound containing a T-cell epitope.
c) In a third step, T-cell activation is determined. Examples of methods suitable for this are detection of cytokine production or secretion by the T cells, of the surface molecule expression on T cells, of target cell lysis or of cell proliferation. Examples of methods suitable for this are a cytokinassay (Chapter 6.2 to 6.24 in Current Protocols in Immunology (1999), edited by Coligan J. E., Kruisbeek A. M., Margulies D. H., Shevach E. M. and Strober W., John Wiley & Sons), ELISPOT (Chapter 6.19 in Current Protocols in Immunology, supra), a $^{51}$Cr release assay (Chapter 3.11 in Current Protocols in Immunology, supra) or detection of proliferation (Chapter 3.12 in Current Protocols in Immunology, supra). Depending on the method used, it is in this connection also possible to distinguish between the immune cells such as cytotoxic T cells, T helper cells, B cells, NK cells, and other cells. The use of inventive compounds, complexes, and/or cells containing the labels of the invention allows detection of T cells recognizing the T-cell epitope via detection of the binding of labeled compounds, complexes and/or cells to the T cells. In a preferred embodiment, binding of inventive MHC-polypeptide complexes to the surface of T cells is detected. This may be carried out such that the MHC complexes are labeled themselves, for example fluorescently labeled, or that, in a further step, an MHC-specific, labeled, for example fluorescently labeled, antibody is used in order to detect in turn the MHC complexes. The fluorescent label of the T cells can then be measured and evaluated, for example, in a fluorescence-activated cell sorter (FACS). Another possibile way of detecting binding of the complexes to the T cells is again measuring T-cell activation (cytokine assay, Elispot, $^{51}$Cr release assay, proliferation, see above). However, this requires simultaneous stimulation of coreceptors (e.g. CD28), for example by coreceptor-specific antibodies (anti-CD28) and/or other unspecific activators (IL-2).

The present invention also relates to a method containing an additional step a') which is introduced after step a").

a') In this additional step a') which follows step a"), the isolated or cultured cells are cocultured with at least one target cell loaded with an inventive compound containing a T-cell epitope, at least one inventive complex containing a T-cell epitope, at least one capsomer, at least one stable capsomer, at least one VLP, at least one CVLP and/or at least one virus, with at least one inventive complex containing a T-cell epitope, and/or at least one target cell presenting a T-cell epitope for at least approx. 8 weeks, in particular for at least approx. 1 week, prior to step b).

Coculturing means growing cells:
  (i) in the presence of at least one target cell loaded with an inventive compound containing a T-cell epitope, at least one inventive complex containing a T-cell epitope, at least one capsomer, at least one stable capsomer, at least one VLP, at least one CVLP, and/or at least one virus,
  (ii) in the presence of at least one inventive complex containing a T-cell epitope,
  (iii) in the presence of at least one target cell presenting a T-cell epitope,
in the same growth medium and the same tissue culture container.

The invention further relates to an assay system (kit) for in vitro detection of the activation of T cells, comprising:
  a) at least one T-cell epitope of the invention, at least one compound of the invention, at least one vector of the invention, at least one cell of the invention, and/or at least one complex of the invention, and
  b) effector cells of the immune system, preferably T cells, in particular cytotoxic T cells or T helper cells.

In a particular embodiment, the assay system is used for determining the L1 protein-specific cytotoxic T cells which are present, for example, in a patient's blood sample or in tumors or lymph nodes of a tumor patient. In this case, the cells described in b) are control cells contained in the assay system, whose activation by the first kit component, the substances mentioned under a), serves as a standard. The activation observed in this reaction is compared with the T-cell activation of cells, which have been isolated from patients, by kit component a).

In a further particular embodiment, the assay system is used, for example, for determining the L1 protein-specific antigenicity of a compound containing a T-cell epitope, a complex containing a T-cell epitope, a capsomer, a stable capsomer, a VLP, a CVLP and/or a virus. In this case, the substances described in a) are control substances whose activating effect on the second kit component, the cells mentioned under b), serves as a standard. The activation observed in this reaction is compared with the activating effect of a compound containing a T-cell epitope, a complex comprising a T-cell epitope, a capsomer, a stable capsomer, a VLP, a CVLP, and/or a virus on kit component b).

The invention further relates to the use of at least one T-cell epitope, at least one inventive compound containing a T-cell epitope, at least one inventive vector containing a nucleic acid coding for a T-cell epitope-containing compound, at least one inventive cell containing a T-cell epitope for, and/or at least one inventive complex containing a T-cell epitope for causing or detecting an immune response.

Suitable cells for immune cell stimulation in vitro as well as in vivo are in particular cells which present at least one of the molecules of the invention via their MHC class I molecules. Examples of cells suitable for antigen presentation are B cells, dendritic cells, macrophages, fibroblasts or other HLA A2.01-positive cells which, by being cultured together with immune cells, can stimulate specific T cells.

In a particular embodiment, it is possible to use a compound of the invention, for example an HPV18 L1E7 fusion protein which additionally contains a T-cell epitope of the invention, for detecting an immune response. Such a compound of the invention may have the ability to form CVLPs.

The invention further relates to a medicament or diagnostic agent which contains at least one inventive compound containing a T-cell epitope, at least one vector containing a nucleic acid coding for a T-cell epitope-containing compound, at least one inventive cell containing a T-cell epitope, and/or at least one inventive complex containing a T-cell epitope and, where appropriate, a pharmaceutically acceptable carrier.

Examples of carriers known to the skilled worker are glass, polystyrene, polypropylene, polyethylene, dextran, nylon, amylase, natural or modified cellulose, polyacrylamides, agarose, aluminum hydroxide or magnetite.

A medicament or diagnostic agent of the invention may be present in solution, bound to a solid matrix, and/or mixed with an adjuvant.

The medicament or diagnostic agent may be administered in different ways. Examples of administration forms known to the skilled worker are parenteral, local and/or systemic administration by, for example, oral, intranasal, intravenous, intramuscular, and/or topical administration. The preferred administration form is influenced, for example, by the natural path of infection of the particular papillomavirus infection. The amount administered depends on the age, weight and general state of health of the patient and the type of papillomavirus infection. The medicament or diagnostic agent may be administered in the form of capsules, a solution, suspension, elixir (for oral administration) or sterile solutions or suspensions (for parenteral or intranasal administration). An inert and immunologically acceptable carrier which may be used is, for example, a saline or phosphate-buffered saline. The medicament is administered in therapeutically effective amounts. These are amounts which are sufficient for causing a protective immunological response.

In a particular embodiment, it is possible to use a compound of the invention, for example an HPV18 L1E7 fusion protein which additionally contains a T-cell epitope of the invention, as medicament or diagnostic agent. Such a compound of the invention may have the ability to form CVLPs.

The figures and the following examples are intended to illustrate the invention in more detail, without restricting it.

FIG. 1 shows the graphical analysis of MTT staining, measured as absorption at 595 nm, of WEHI-cell lysates which had been incubated with supernatants of T cells which in turn had been stimulazed by different, antigen-presenting peripheral blood lymphocytes (PBLs). T cells stimulated by specific, antigen-presenting PBLs release TNFα. This induces apoptosis in WEHI cells so that these cells are no longer able to process MTT into a brownish dye. Low absorption means low dye production and thus many apoptotic cells which had thus been exposed to a lot of TNFα so that the corresponding T cells had been stimulated. Thus, stimulation of T cells improves with decreasing absorption at 595 nm for a particular antigen.

Figure 2:
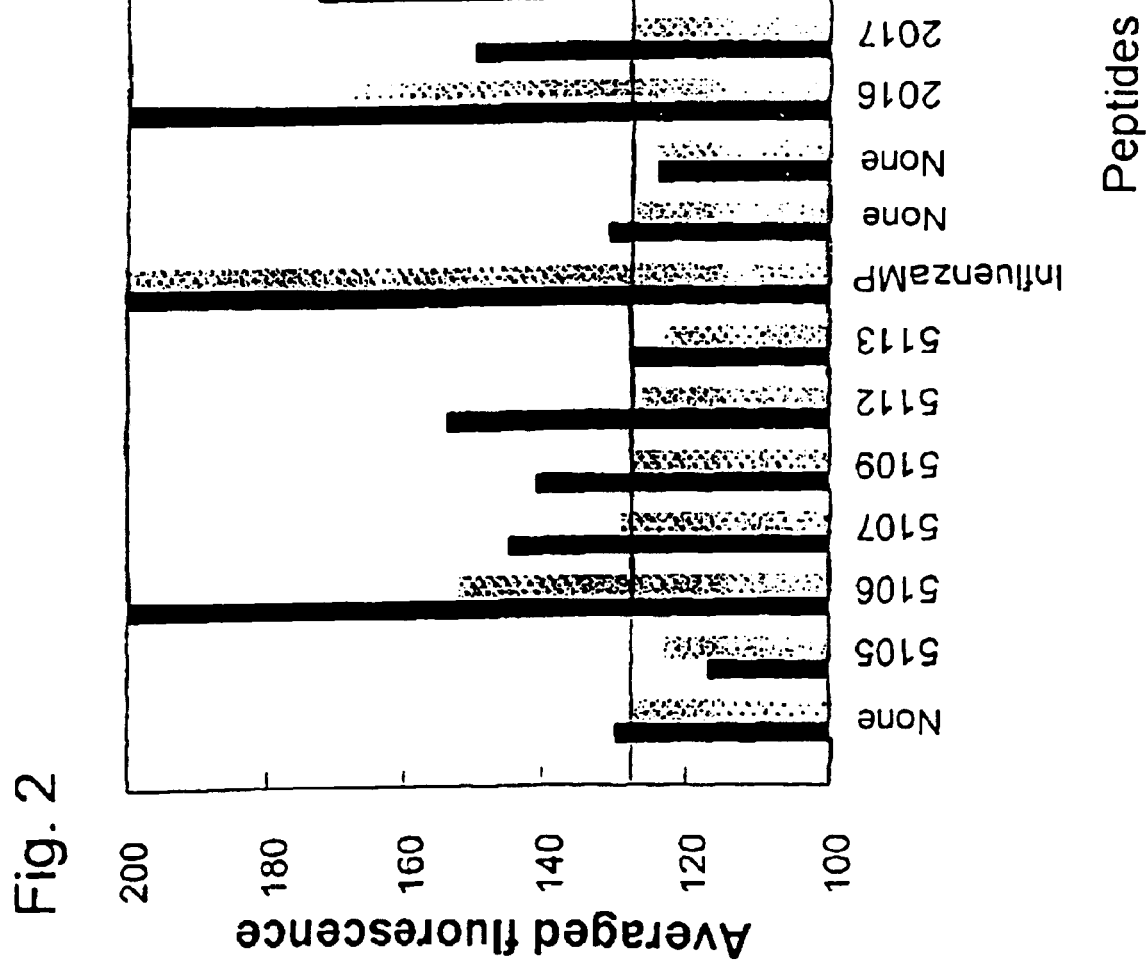

FIG. 2 shows the graphical analysis of the fluorescence, measured in an FACS analysis, of T2 cells whose MHC-1 molecules located on the cell surface had been labeled with an FITC-labeled antibody. Cells whose MHC-1 molecules can specifically bind those peptides listed on the X axis, have an increased number of MHC-1 molecules, since the specific binding stabilizes the MHC complexes so that they can accumulate on the cell surface.

Figure 3:
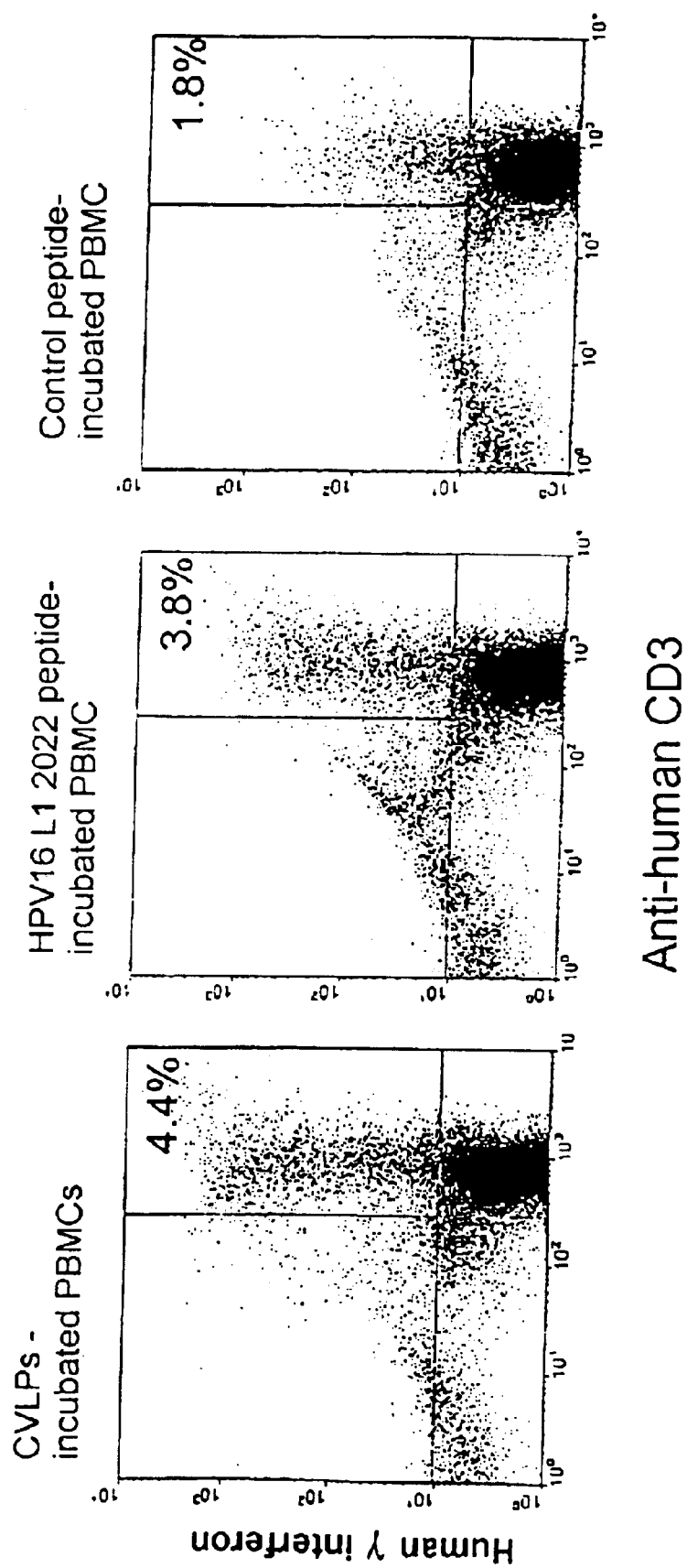

FIG. 3 shows the analysis of three FACScan experiments after restimulating CVLP-specific human T cells with peripheral blood mononuclear cells (PBMCs) which present different antigens. The content of T cell-specific CD3 for each experiment is listed from left to right and the content of human γ interferon which is specific for activated cells is listed from bottom to top.

Figure 4:
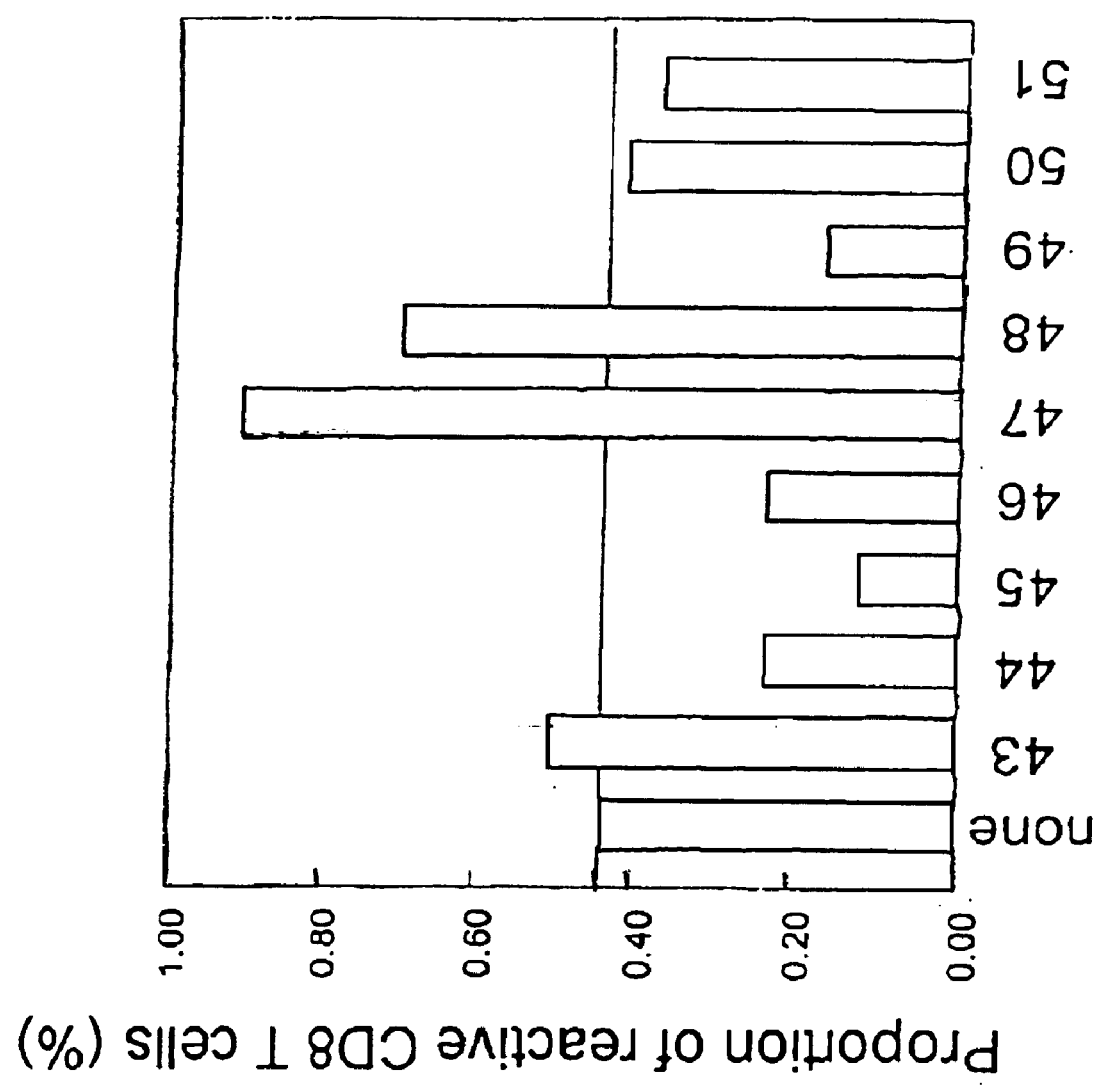

FIG. 4 shows the analysis of FACScan experiments after restimulating specific human T cells of an HLA A1-positive donor with peripheral blood mononuclear cells (PBMCS) which present different antigens. The name of the particular peptide with which the PBMCs were loaded is listed from left to right. "None" represents PBMCs which were incubated only with buffer. The Y axis shows the proportion of CD8-positive T cells which were classified as reactive in the FACScan experiment on the basis of γ-interferon expression.

Figure 5:
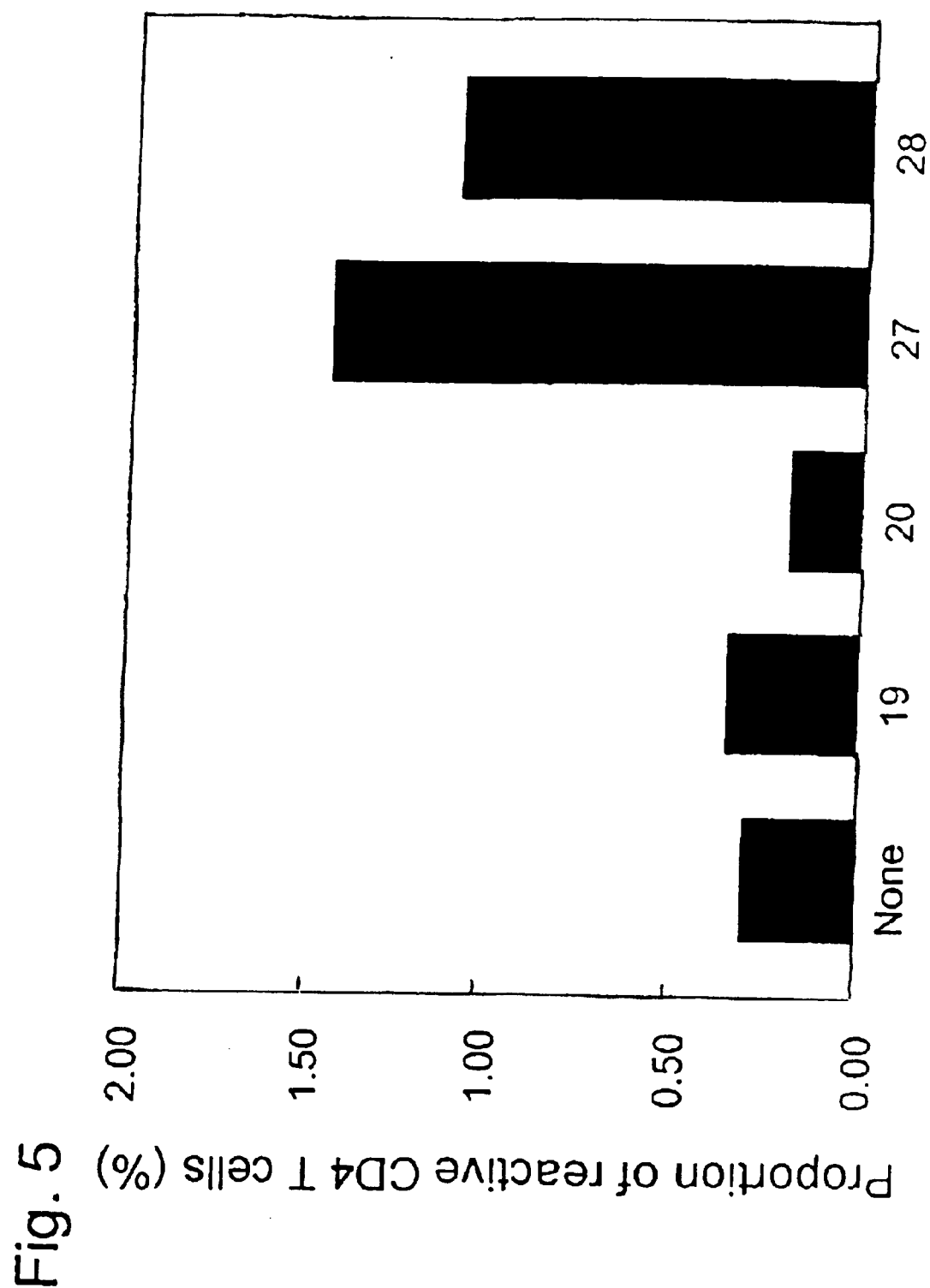

FIG. 5 shows the analysis of FACScan experiments after restimulating specific human T cells of a non-HLA-classified donor with peripheral blood mononuclear cells (PBMCs) which present different antigens. The name of the particular peptide with which the PBMCs were loaded is listed from left to right. "None" represents PBMCs which were incubated only with buffer. The Y axis shows the proportion of CD4-positive T cells which were classified as reactive in the FACScan experiment on the basis of γ-interferon expression.

Figure 6:
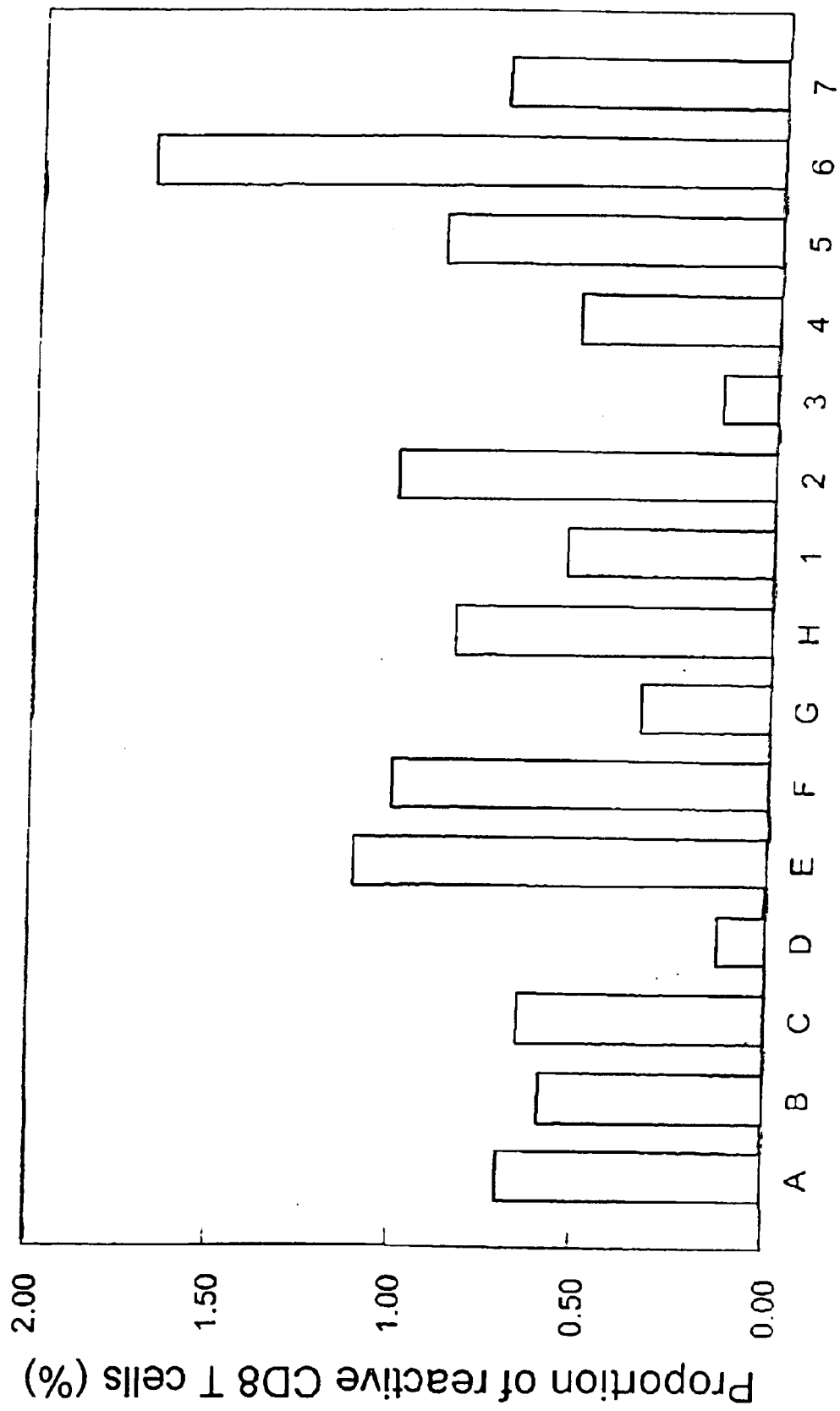

FIG. 6 shows the analysis of FACScan experiments after restimulating specific human T cells of an HLA A1-positive donor with peripheral blood mononuclear cells (PBMCS) which present different antigens. The name of the particular peptide pool with which the PBMCs were loaded is listed from left to right. "None" represents PBMCs which were incubated only with buffer. The Y axis shows the proportion of CD8-positive T cells which were classified as reactive in the FACScan experiment on the basis of γ-interferon expression.

Figure 7:
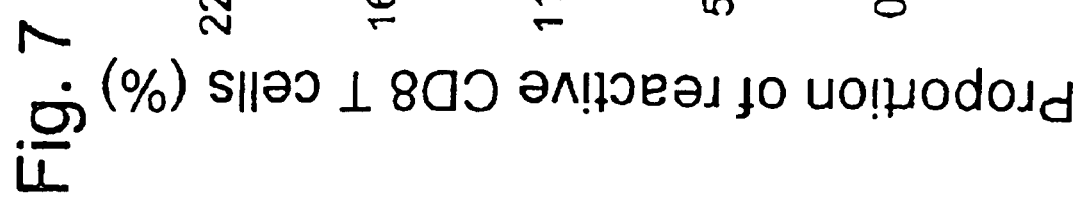

FIG. 7 shows the analysis of FACScan experiments after restimulating specific human T cells of an HLA A24-positive donor with peripheral blood mononuclear cells (BLCLS) which present different antigens. The name of the particular peptide pool with which the BLCLs were loaded is listed from left to right. "None" represents BLCLs which were incubated only with buffer. The Y axis shows the proportion of CD8-positive T cells which were classified as reactive in the FACScan experiment on the basis of γ-interferon expression.

Figure 8:
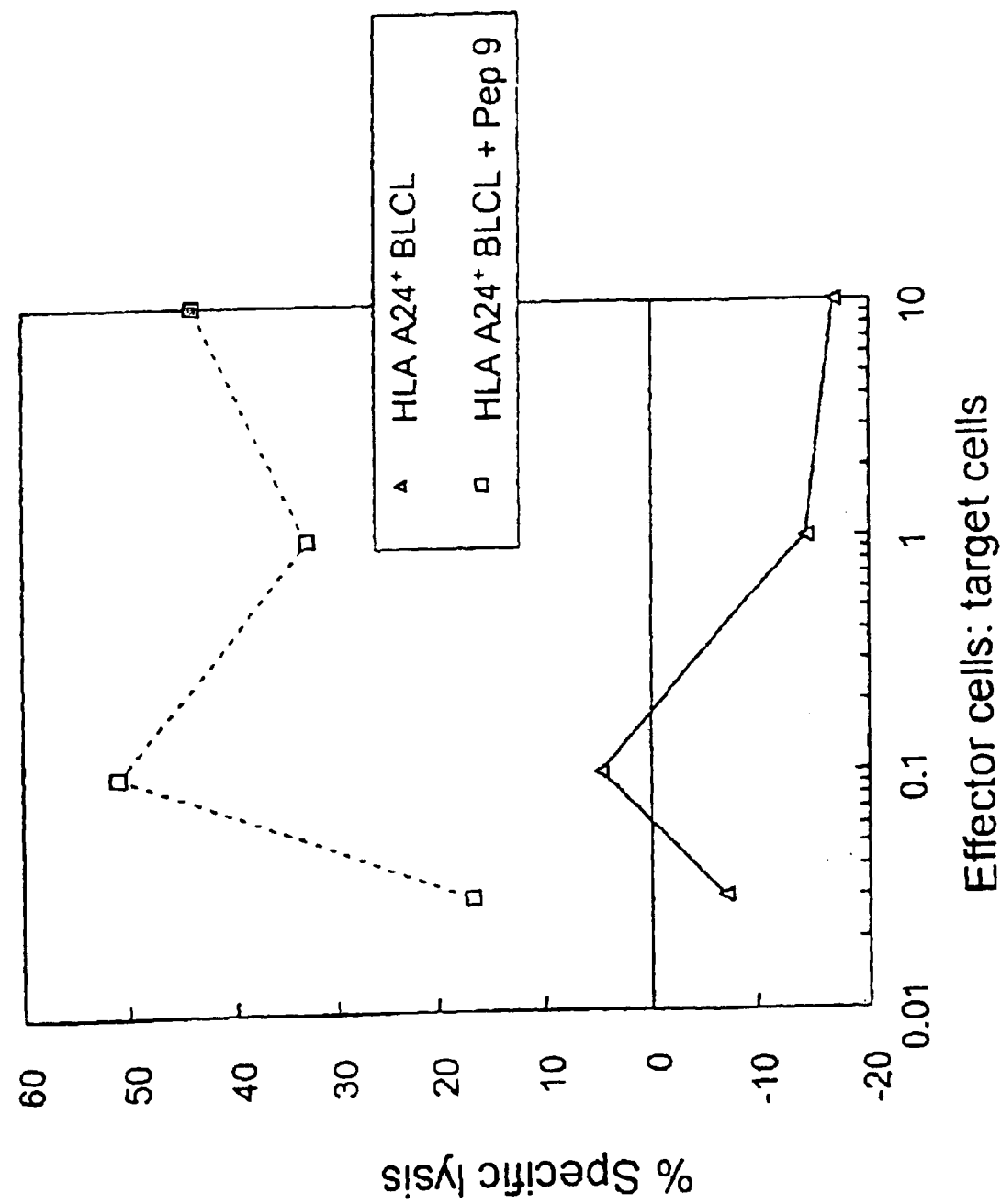

FIG. 8 shows the analysis of a $^{51}$Cr release experiment after loading BLCL cells of an HLA A24-positive donor (=target cells) with peptide 9. The target cells were lysed by T cells stimulated with peptides 1–43 (=effector cells). The X axis shows the ratio of the effector cells used to the target cells used, and the Y axis shows the % of specifically lysed target cells, determined by $^{51}$Cr release from the target cells. The % values were calculated according to the formula given in Example 7.

EXAMPLES

1. Description of Starting Materials

The preparation of HPV16 L1$_{AC}$·E7$_{1-55}$ CVLPs was carried out according to the German patent application DE 198 12 941, see also Müller M. et al. (1997) Virology 234, 93–111.

The preparation of L1 VLPs was carried out according to M üller M. et al. (1997) Virology 234, 93–111.

T2 cells which can be obtained under ATCC number: CRL-1992 have a defect in the antigen processing-associated transport, which stops the loading of MHC-1 molecules in the endoplasmic reticulum. The unloaded MHC-1 molecules which are nevertheless present on the cell surface may be loaded, for example, by incubating the cells in peptide-containing media so that these cells are very suitable for presenting an antigen.

WEHI cells can be obtained under ATCC number CRL-2148.

PMBC means peripheral blood mononuclear cells whose isolation is described, for example, in Rudolf M. P. et al. (1999), Biol. Chem. 380, 335–40.

BLCL means a B-cell line transformed with the aid of Epstein-Barr virus (obtained from Dr. Andreas Kaufmann, Friedrich-Schiller University, Jena, Germany).

BB7.2 means an α-HLA A2.01-specific monoclonal mouse antibody (ATCC HB-82).

α-hum CD28 means a monoclonal mouse antibody which is directed against the extracellular part of human CD28.

α-hum CD3/PE means a monoclonal mouse antibody which is directed against the extracellular part of human CD3 (E) and contains the fluorescent marker phycoerythrin (Medac, Hamburg, Germany).

α-hum CD4/Cychrome means a monoclonal mouse antibody which is directed against the extracellular part of human CD4 and contains the fluorescent marker Cychrome (DAKO; Glostrup, Denmark).

α-hum γ Interferon/FITC means a monoclonal rat antibody which is directed against human γ interferon and contains the fluorescent marker FITC (Medac, Hamburg, Germany).

α-hum CD8/PE means a monoclonal mouse antibody which is directed against the extracellular part of human CD8 and contains the fluorescent marker phycoerythrin (Pharmingen, Heidelberg, Germany).

InfluenzaMP means amino acids 58–66 GILGFVFTL of the influenza matrix protein (see Dunbar P. R. et al. (1998) Curr. Biol. 26, 413–6).

HPV16E7 peptide means amino acids 11–20 YMLDLQ-PETT of human papillomavirus E7 protein.

On the basis of the algorithm for potential HLA A2.01-binding peptides (Parker, K C et al. (1994) J. Immunol.

152:163), carried out in the peptide prediction program by Parker under http://www-bimas.dcrt.nih.gov/molbio/hla_bind/index.html, the peptides below were identified as candidates for HPV16 L1 and synthesized. The stated amino acid positions of the particular peptide are shown in relation to Met(+1) of the L1 sequence deposited under GenBank accession number k0271B (see Table 1 below).

Table 1: Potential HLA A2.01-binding Pptides of HPV16 L1

| Peptide name | Sequence | Relative L1 position |
|---|---|---|
| 5104 | ILVPKVSGL | (86–94) (SEQ ID NO: 1) |
| 5105 | SMDYKQTQL | (174–182) (SEQ ID NO: 20) |
| 5106 | RLVWACVGV | (123–131) (SEQ ID NO: 2) |
| 5107 | HLFNRAGTV | (285–293) (SEQ ID NO: 3) |
| 5108 | YLRREQMFV | (275–283) (SEQ ID NO: 4) |
| 5109 | TLQANKSEV | (238–246) (SEQ ID NO: 5) |
| 5112 | ILEDWNFGL | (426–434) (SEQ ID NO: 6) |
| 5113 | TLEDTYRFV | (441–449) (SEQ ID NO: 21) |
| 2016 | SLWLPSEATVYL | (28–39) (SEQ ID NO: 7) |
| 2017 | NLASSNYFPT | (311–320) (SEQ ID NO: 8) |
| 2018 | TLTADVMTYI | (408–417) (SEQ ID NO: 9) |
| 2019 | YLPPVPVSKV | (38–47) (SEQ ID NO: 10) |
| 2020 | YDLQFIFQL | (396–404) (SEQ ID NO: 11) |
| 2021 | FQLCKITLT | (402–410) (SEQ ID NO: 22) |
| 2022 | ICWGNQLFV | (349–357) (SEQ ID NO: 12) |
| 2023 | KVVSTDEYV | (46–54) (SEQ ID NO: 23) |
| 2024 | QLFVTVVDT | (354–362) (SEQ ID NO: 24) |
| 2025 | GLQYRVFRI | (93–101) (SEQ ID NO: 25) |

Furthermore, 20 mer peptides which overlap by in each case 9 amino acids and which include the sequence of HPV16 L1 and E7 proteins were synthesized. The peptides were numbered consecutively from 1 to 52.

Their name and their sequence are summarized in the following table in which "restr." means restricted.

Table 2: Synthetic Overlapping 20 mer Peptides of HPV16 L1 and E7

| Peptid Name | Sequence | relative Position | Epitop-Information |
|---|---|---|---|
| L1-Peptide | | | |
| 1 | MSLWLPSEATVYLPPVPVSK | (1–20) | (SEQ ID NO: 26) |
| 2 | YLPPVPVSKVVSTDEYVART | (12–31) | (SEQ ID NO: 27) |
| 3 | STDEYVARTNIYYHAGTSRL | (23–42) | (SEQ ID NO: 28) |
| 4 | YYHAGTSRLLAVGHPYFPIK | (34–53) | (SEQ ID NO: 29) |
| 5 | VGHPYFPIKKPNNNKILVPK | (45–64) | (SEQ ID NO: 30) |
| 6 | NNNKILVPKVSGLQYRVFRI | (56–75) | (SEQ ID NO: 31) |
| 7 | GLQYRVFRIHLPDPNKFGFP | (67–86) | (SEQ ID NO: 32) |
| 8 | PDPNKFGFPDTSFYNPDTQR | (78–97) | (SEQ ID NO: 33) |
| 9 | SFYNPDTQRLVWACVGVEVG | (89–108) | (SEQ ID NO: 34) cytotoxic epitope HLA A24 restr. |
| 10 | WACVGVEVGRGQPLGVGISG | (100–119) | (SEQ ID NO: 35) |
| 11 | QPLGVGISGHPLLNKLDDTE | (111–130) | (SEQ ID NO: 36) |
| 12 | LLNKLDDTENASAYAANAGV | (122–141) | (SEQ ID NO: 37) |
| 13 | SAYAANAGVDNRECISMDYK | (133–152) | (SEQ ID NO: 38) |
| 14 | RECISMDYKQTQLCLIGCKP | (144–163) | (SEQ ID NO: 39) |
| 15 | QLCLIGCKPPIGEHWGKGSP | (155–174) | (SEQ ID NO: 40) |
| 16 | GEHWGKGSPCTNVAVNPGDC | (166–185) | (SEQ ID NO: 41) |
| 17 | NVAVNPGDCPPLELINTVIQ | (177–196) | (SEQ ID NO: 42) |
| 18 | LELINTVIQDGDMVDTGFGA | (188–207) | (SEQ ID NO: 43) |
| 19 | DMVDTGFGAMDFTTLQANKS | (199–218) | (SEQ ID NO: 44) |
| 20 | FTTLQANKSEVPLDICTSIC | (210–229) | (SEQ ID NO: 45) |
| 21 | PLDICTSICKYPDYIKMVSE | (221–240) | (SEQ ID NO: 46) |
| 22 | PDYIKMVSEPYGDSLFFYLR | (232–251) | (SEQ ID NO: 47) |
| 23 | GDSLFFYLRREQMFVRHLFN | (243–262) | (SEQ ID NO: 48) |
| 24 | QMFVRHLFNRAGAVGENVPD | (254–273) | (SEQ ID NO: 49) |
| 25 | GAVGENVPDDLYIKGSGSTA | (265–284) | (SEQ ID NO: 50) |
| 26 | YIKGSGSTANLASSNYFPTP | (276–295) | (SEQ ID NO: 51) |
| 27 | ASSNYFPTPSGSMVTSDAQI | (287–306) | (SEQ ID NO: 52) T-helper epitope |
| 28 | SMVTSDAQIFNKPYWLQRAQ | (298–317) | (SEQ ID NO: 53) T-helper epitope |
| 29 | KPYWLQRAQGHNNGICWGNQ | (309–328) | (SEQ ID NO: 54) |
| 30 | NNGICWGNQLFVTVVDTTRS | (320–339) | (SEQ ID NO: 55) |
| 31 | VTVVDTTRSTNMSLCAAIST | (331–350) | (SEQ ID NO: 56) |
| 32 | MSLCAAISTSETTYKNTNFK | (342–361) | (SEQ ID NO: 57) |
| 33 | TTYKNTNFKEYLRHGEEYDL | (353–372) | (SEQ ID NO: 58) |
| 34 | LRHGEEYDLQFIFQLCKITL | (364–383) | (SEQ ID NO: 59) |
| 35 | IFQLCKITLTADVMTYIHSM | (375–394) | (SEQ ID NO: 60) |
| 36 | DVMTIHSMNSTILEDWNFG | (386–405) | (SEQ ID NO: 61) |
| 37 | TILEDWNFGLQPPPGGTLED | (397–416) | (SEQ ID NO: 62) |
| 38 | PPPGGTLEDTYRFVTSQAIA | (408–427) | (SEQ ID NO: 63) |
| 39 | RFVTSQAIACQKHTPPAPKE | (419–438) | (SEQ ID NO: 64) |
| 40 | KHTPPAPKEDPLKKYTFWEV | (430–449) | (SEQ ID NO: 65) |
| 41 | LKKYTFWEVNLKEXFSADLD | (441–460) | (SEQ ID NO: 66) |
| 42 | KEKFSADLDQFPLGRKFLLQ | (452–471) | (SEQ ID NO: 67) |
| 43 | PLGRKFLLQAGMHGDTPTLH | (463–482) | (SEQ ID NO: 68) cytotoxic epitope HLA A1 restr. |
| E7 Peptides | | | |
| 44 | MHGDTPTLHEYMLDLQPETT | (1–20) | (SEQ ID NO: 69) |
| 45 | MLDLQPETTDLYCYEQLNDS | (12–31) | (SEQ ID NO: 70) |
| 46 | YCYEQLNDSSEEEDEIDGPA | (23–42) | (SEQ ID NO: 71) |
| 47 | EEDEIDGPAGQAEPDRAHYN | (34–53) | (SEQ ID NO: 72) |
| 48 | AEPDRAHYNIVTFCCXCDST | (45–64) | (SEQ ID NO: 73) |
| 49 | TFCCKCDSTLRLCVQSTHVD | (56–75) | (SEQ ID NO: 74) |
| 50 | LCVQSTHVDIRTLEDLLMGT | (67–86) | (SEQ ID NO: 75) |
| 51 | TLEDLLMGTLGIVCPICSQKP | (78–97) | (SEQ ID NO: 76) |
| Influenza control peptide | | | |
| 52 | KEYLRHGEEGILGFVFTLCK | | (SEQ ID NO: 77) |

Golgi Plug is obtainable through Pharmingen (Hamburg, Germany).

Monensin is obtainable through Sigma (Deisenhofen, Germany).

IL-2 was obtained from Becton Dickinson (Hamburg, Germany).

MTT solution in PBS means 2.5 mg/ml 3-[4,5-dimethylthiazol-2-yl]-2,5-diphenyltetrazolium bromide in PBS (Sigma, Deisenhofen, Germany).

PBS means phosphate-buffered saline and consists of 16.6 MM $Na_2HPO_4$ 8.4 mM $NaH_2PO_4$, 150 mM NaCl pH 7.4.

Cells were cultured in each case at 37° C. and 5% $CO_2$ in RPMI medium (Gibco BRL, Eggenstein; Germany) with 10% fetal calf serum, kanamycin and ampicillin.

Luma plates and the Canberra-Packerd B-plate counter were obtained from Canberra-Packerd, Dreieich, Germany.

FACScan calibur means fluorescence-activated cell sorter; the apparatus was obtained from Becton Dickenson (Hamburg, Germany).

Cellquest software was obtained from Becton Dickinson (Hamburg, Germany).

2. Peptide-specific TNFα Secretion by CVLP-stimulated T Cells a) Preparation of CVLP-specific T Cells Human T cells ($4 \times 10^5$) of an HLA A2.01-positive donor were stimulated with HPV16 $L1_{AC}·E7_{1-55}$ CVLPs at 37° C. for 8 weeks with weekly addition of 1 μg/ml CVLPs, $10^5$ irradiated peripheral blood mononuclear cells (PMBCs) and 10 IU/ml IL-2, and harvested.

b) Stimulation with Antigens

The cells were stimulated in 100 μl of medium at 37° C. overnight with different antigens (PMBC+E7 peptide;

PMBC+HPV16 L1$_{\alpha C}$·E7$_{1-55}$ (CVLP); PMBC+5104, 5105, 5106, 5107, 5108, 5109, 5112, 5113, 10 µg/ml each) in the presence of 10 IU/ml IL-2. During this time, stimulated cells produce TNFα.

c) Detection of TNFα

The following day, 50 µl of supernatant were removed, frozen, thawed again (in order to destroy possibly coremoved cells) and added to 50 µl of a cell suspension containing 0.9×10$^6$ WEHI cells, 2 µg/ml actinomycin D and 400 mM LiCl. The cells were incubated at 37° C. for 24 h. During this time, TNFα (if present in the supernatant) induces apoptosis of WEHI cells. Addition of 50 µl of a 2.5 mg/ml MTT solution in PBS stained non-apoptotic cells brown within three hours, whereas apoptotic cells remained yellow. All cells were lysed by adding 100 µl of lysis buffer (34% N,N-dimethylformamide, 20% sodium dodecyl sulfate) and incubating at 37° for at least 6 hours so that the dyes were released. Finally, absorption of the solution was measured at 595 nm.

FIG. 1 shows the absorption measured at 595 nm as a function of the different antigens. Low absorption means low dye production and thus many apoptotic cells which had thus been exposed to a lot of TNFα so that the corresponding T cells had been stimulated. Thus, T-cell stimulation improved with decreasing absorption at 595 nm.

Result: peptides 5104, 5106, 5107, 5108, 5109 and 5112 were capable of stimulating CVLP-specific T cells.

3. Binding of Peptides to T2 Cells a) Loading of T2 Cells 2.5×10$^6$ T2 cells of an HLA A2.01-positive donor were incubated in medium containing 2% human serum at 37° C. overnight in the presence of 0, 10 or 100 µg/ml 5105, 5106, 5107, 5109, 5112, 5113, InfluenzaMP, 2016, 2017, 2018, 2019, 2020, 2021, 2022, 2023, 2024, 2025 peptide. During this time, fitting peptides can bind to the unphysiologically empty MHC-1 molecules and thus stabilize said molecules, whereas MHC-1 molecules without fitting peptides are relatively quickly reabsorbed into the cell. Thus, specifically binding peptides increase the number of MHC-1 molecules on the cell surface.

b) Detection of Peptide Binding to MHC-1 Complexes of T2 Cells

The following morning, the cells were harvested, washed with PBS containing 0.5% bovine serum albumin (BSA) and the MHC-1 molecules were detected. This is carried out by incubating with antibody BB7.2 on ice for 30 min, washing and staining with an α-mouse FITC antibody on ice for a further 30 min. The cells were washed again, measured in a FACScan calibur and analyzed using Cellquest software.

FIG. 2 shows the measured fluorescence as a function of the various peptides.

Result: T2 cells, after incubation with L1 peptides 5106, 5107, 5109, 5112, 2016, 2017, 2018, 2019, 2020 and 2022 show, as after incubation with the known influenza peptide MP, significantly more MHC molecules on the cell surface, indicating binding of the corresponding peptides to the MHC molecules.

4. Restimulation of CVLP-stimulated T Cells with Different Antigen-presenting Cells Human T cells (4×10$^5$) of an HLA A2.01-positive donor were stimulated with HPV16 L1$_{AC}$·E7$_{1-55}$ CVLPs at 37° C. for 8 weeks with weekly addition of 1 µg/ml CVLPs and 10$^5$ antigen-presenting cells (irradiated PMBCs), and harvested. The cells were then restimulated in 100 µl of medium at 37° C. with 10 µg/ml various antigens in the presence of 10 IU/ml IL2 and 0.5 µg/ml α-human CD28:

a) with CVLP-incubated PBMCs overnight b) with L1 2022 peptide-incubated PBMCs overnight c) with L1 2025 peptide (control peptide)incubated PBMCs overnight After one hour, 1 µl of Golgi Plug was added. The cells were incubated at 37° C. for a further 5 hours. The cells were then fixed and permeabilized, and stained with α-hum CD3/PE, with α-hum CD4/Cychrome and with α-hum γ-interferon/FITC. The cells were examined in a FACScan calibur with respect to their label and the data were analyzed with the aid of Cellquest software.

Result: FIG. 3 shows that CVLP-incubated PBMCs as well as L1 peptide 2022-incubated PBMCs, but not control peptide-incubated PBMCs, effected restimulation of CVLP-stimulated T cells.

5. Restimulation of CVLP-stimulated T Cells with Different Antigen-presenting Cells Human T cells (4×10$^5$) of an HLA A1-positive donor were stimulated with HPV16 L1$_{AC}$·E7$_{1-55}$ CVLPs at 37° C. for 5 weeks with weekly addition of 1 µg/ml CVLPs and 10$^5$ antigen-presenting cells (irradiated PMBCs), and harvested. The cells were then restimulated in 100 µl of medium at 37° C. with 10 µg/ml of the peptides listed along the X axis of FIG. 4 in the presence of 10 IU/ml IL2. Cells incubated only with buffer served as a negative control.

After one hour, 1 µl of Monensin (300 µM) was added. The cells were incubated at 37° C. for a further 5 hours. The cells were then fixed and permeabilized, and stained with α-hum CD8/PE, with α-hum CD4/Cychrome and with α-hum γ-interferon/FITC. The cells were examined in a FACScan calibur with respect to their label and the data were analyzed with the aid of Cellquest software.

Result: FIG. 4 shows that PBMCs incubated with peptides 43, 47 and 48, but not PBMCs incubated with the remaining peptides, effected restimulation of CVLP-stimulated T cells. Peptide 43 contains the 9 mer peptide of the sequence MHGDTPTLH (SEQ ID NO: 14), and the two overlapping peptides 47 and 48 contain the 10 mer peptide of the sequence QAEPDRAHYN (SEQ ID NO: 16), which in each case have been described as HLA A1-binding peptides in Kast et al. (supra), but for which it has been impossible so far to carry out a functional detection.

6. Restimulation of CVLP-stimulated T Cells with Different Antigen-presenting Cells Human T cells (4×10$^5$) of a non-HLA-classified donor were stimulated with HPV16 L1$_{AC}$·E7$_{1-55}$ CVLPs at 37° C. for 6 weeks with weekly addition of 1 µg/ml CVLPs and 10$^5$ antigen-presenting cells (irradiated PMBCs), and harvested. The cells were then restimulated in 100 µl of medium at 37° C. with 10 µg/ml of the peptides listed along the X axis of FIG. 5 in the presence of 10 IU/ml IL2. Cells incubated only with buffer served as a negative control.

After one hour, 1 µl of Monensin (300 µM) was added. The cells were incubated at 37° C. for a further 5 hours. The cells were then fixed and permeabilized, and stained with α-hum CD8/PE, with α-hum CD4/Cychrome and with α-hum γ-interferon/FITC. The cells were examined in a FACScan calibur with respect to their label and the data were analyzed with the aid of Cellquest software.

Result FIG. 5 shows that PBMCs incubated with peptides 27 and 28, but not PBMCs incubated with the remaining peptides, effected restimulation of CVLP-stimulated T cells.

The two overlapping peptides 27 and 28 contain the peptide of the sequence SMVTSDAQI (SEQ ID NO: 17) so that the actually recognized peptide essentially must include this sequence.

7. Restimulation of CVLP-stimulated T Cells with Different Antigen-presenting Cells Human T cells ($4\times10^5$) of an HLA A1-positive donor were stimulated with HPV16 $L1_{AC} \cdot E7_{1-55}$ CVLPs at 37° C. for 6 weeks with weekly addition of 1 µg/ml CVLPs and $10^5$ antigen-presenting cells (irradiated PMBCs), and harvested.

The 20 mer peptides 1 to 51 were combined in peptide pools A to H and 1 to 7 according to the matrix

| Pools | A | B | C | D | E | F | G | H |
|-------|---|---|---|---|---|---|---|---|
| 1 | 1 | 2 | 3 | 4 | 5 | 6 | 7 | 8 |
| 2 | 9 | 10 | 11 | 12 | 13 | 14 | 15 | 16 |
| 3 | 17 | 18 | 19 | 20 | 21 | 22 | 23 | 24 |
| 4 | 25 | 26 | 27 | 28 | 29 | 30 | 31 | 32 |
| 5 | 33 | 34 | 35 | 36 | 37 | 38 | 39 | 40 |
| 6 | 41 | 42 | 43 | 44 | 45 | 46 | 47 | 48 |
| 7 | 49 | 50 | 51 | | | | | |

The T cells of an HLA A1-positive donor were then restimulated in 100 µl of medium at 37° C. with the peptide pools in the presence of 10 IU/ml IL2. In this connection, such amounts of peptide pools were used that for each individual peptide 1 µg/ml was added. Cells incubated only with buffer served as a negative control.

After one hour, 1 µl of Golgi Plug was added. The cells were incubated at 37° C. for a further 5 hours. The cells were then fixed and permeabilized, and stained with α-hum CD8/PE, with α-hum CD4/Cychrome and with α-hum γ-interferon/FITC. The cells were examined in a FACScan calibur with respect to their label and the data were analyzed with the aid of Cellquest software.

Result: FIG. 6 shows that PBMCs incubated with peptide pools E and 6, but not PBMCs incubated with the remaining peptide pools, effected restimulation of CVLP-stimulated T cells. Peptide pools E and 6 both contain peptide 45 which thus is in all probability responsible for restimulation of CVLP-stimulated T cells. Peptide 45 in turn contains: peptide ETTDLYCY (SEQ ID NO: 15) which has been described as HLA A1-binding peptide by Kast et al. (supra), but for which it has been impossible so far to carry out a functional detection.

Furthermore, the T cells of an HLA A24-positive donor were restimulated with the peptide pools as above and analyzed.

Result: FIG. 7 shows that PBMCs incubated with peptide pools A and 2, but not PBMCs incubated with the remaining peptide pools, effected restimulation of CVLP-stimulated T cells. Peptide pools A and 2 both contain peptide 9 which thus is in all probability responsible for restimulation of CVLP-stimulated T cells. The prediction according to Parker et al. (supra) results in a potential peptide for HLA A24 which has the sequence FYNPDTQRL (SEQ ID NO: 13) and is thus probably responsible for the activity of peptide 9.

8. Lysis of BLCL Cells Loaded with Peptide 9

BLCL cells of an HLA A24-positive donor were incubated with $^{15}$Cr at 37° C. for one hour, washed three times with medium and divided into 2 aliquots. 10 µg/ml of peptide 9 were added to one aliquot of the cells, and the other aliquot served as a negative control in the absence of a peptide. Subsequently, in each case 2000 cells (=target cells) were added to increasing amounts of T cells (=effector cells) in a total volume of 150 µl. The T cells had been stimulated previously over 5 weeks with a mixture of 43 peptides (peptides 1–43, 1 µg/ml each). Reaction mixtures for spontaneous and maximum cell lysis were set up in parallel. For spontaneous lysis, target cells which were incubated in medium were used, and for maximum lysis target cells which were incubated with 0.5% Triton were used. The mixtures were incubated at 37° C. for 5 h. 50 µl of mixture supernatant were applied to Luma plates and dried at room temperature overnight. On the following morning, the amount of radioactive $^{51}$Cr was determined with the aid of a Canberra-Packerd B-plate counter (counts) and compared to the maximal lysed cells of the Triton mixture. The percentage of specific lysis was determined according to the formula:

$$x=100 \cdot (\text{counts} - \text{spontaneous counts})/(\text{maximal counts} - \text{spontaneous counts}).$$

FIG. 8 shows that it was possible for the T cells to lyse BLCL cells loaded with peptide 9 effectively, but not unloaded BLCL cells. Peptide 9 is thus an HLA A24-restricted cytotoxic T-cell epitope.

---

What is claimed is:

1. A cytotoxic T-cell epitope consisting of an amino acid sequence ICWGNQLFV (SEQ ID NO: 12).

\* \* \* \* \*

UNITED STATES PATENT AND TRADEMARK OFFICE
CERTIFICATE OF CORRECTION

PATENT NO. : 6,838,084 B1
APPLICATION NO. : 09/980177
DATED : January 4, 2005
INVENTOR(S) : Jochmus et al.

It is certified that error appears in the above-identified patent and that said Letters Patent is hereby corrected as shown below:

Column 8, line 58, replace "width" with --with--.

Column 13,
    Line 36, replace "(PBMCS)" with -- (PBMCs) --;
    Line 55, replace "(PBMCS)" with -- (PBMCs) --; and
    Line 65, replace "(BLCLS)" with -- (BLCLs) --.

Column 14,
    Line 22, delete "M"; and
    Line 23, replace "üller" with --Müller--.

Column 15,
    Line 8, replace "P ptides" with --Peptides--;
    Line 40, Table 2, replace "Pep-tid" with --Pep-tide--; and
    Line 40, Table 2, replace "Epitop-" with --Epitope--.

Column 16,
    Line 4, Table 2, replace "Pep-tid" with --Pep-tide--;
    Line 4, Table 2, replace "Epitop-" with --Epitope--;
    Line 27, after "(SEQ ID NO:70)", insert --cytotoxic epitope HLA A1 restr.--;
    Line 29, after "(SEQ ID NO:72)", insert --cytotoxic epitope HLA A1 restr.--;
    Line 30, after "(SEQ ID NO:73)", insert --cytotoxic epitope HLA A1 restr.--; and
    Line 46, replace "MM" with --mM--.

Column 17, line 1, replace "$L1_{\alpha C} \cdot E7_{1-55}$" with --$L1_{\Delta c} \cdot E7_{1-55}$--.

Column 18, line 3, replace "peptide)incubated" with --peptide) -incubated--.

UNITED STATES PATENT AND TRADEMARK OFFICE
CERTIFICATE OF CORRECTION

PATENT NO. : 6,838,084 B1
APPLICATION NO. : 09/980177
DATED : January 4, 2005
INVENTOR(S) : Jochmus et al.

It is certified that error appears in the above-identified patent and that said Letters Patent is hereby corrected as shown below:

Column 20, line 24, replace "cells). were" with --cells) were--.

Signed and Sealed this

Twenty-sixth Day of June, 2007

JON W. DUDAS
*Director of the United States Patent and Trademark Office*

SEQUENCE LISTING

```
<160> NUMBER OF SEQ ID NOS: 77

<210> SEQ ID NO 1
<211> LENGTH: 9
<212> TYPE: PRT
<213> ORGANISM: Human papillomavirus type 16

<400> SEQUENCE: 1

Ile Leu Val Pro Lys Val Ser Gly Leu
1               5

<210> SEQ ID NO 2
<211> LENGTH: 9
<212> TYPE: PRT
```

-continued

<213> ORGANISM: Human papillomavirus type 16

<400> SEQUENCE: 2

Arg Leu Val Trp Ala Cys Val Gly Val
1               5

<210> SEQ ID NO 3
<211> LENGTH: 9
<212> TYPE: PRT
<213> ORGANISM: Human papillomavirus type 16

<400> SEQUENCE: 3

His Leu Phe Asn Arg Ala Gly Thr Val
1               5

<210> SEQ ID NO 4
<211> LENGTH: 9
<212> TYPE: PRT
<213> ORGANISM: Human papillomavirus type 16

<400> SEQUENCE: 4

Tyr Leu Arg Arg Glu Gln Met Phe Val
1               5

<210> SEQ ID NO 5
<211> LENGTH: 9
<212> TYPE: PRT
<213> ORGANISM: Human papillomavirus type 16

<400> SEQUENCE: 5

Thr Leu Gln Ala Asn Lys Ser Glu Val
1               5

<210> SEQ ID NO 6
<211> LENGTH: 9
<212> TYPE: PRT
<213> ORGANISM: Human papillomavirus type 16

<400> SEQUENCE: 6

Ile Leu Glu Asp Trp Asn Phe Gly Leu
1               5

<210> SEQ ID NO 7
<211> LENGTH: 12
<212> TYPE: PRT
<213> ORGANISM: Human papillomavirus type 16

<400> SEQUENCE: 7

Ser Leu Trp Leu Pro Ser Glu Ala Thr Val Tyr Leu
1               5                   10

<210> SEQ ID NO 8
<211> LENGTH: 10
<212> TYPE: PRT
<213> ORGANISM: Human papillomavirus type 16

<400> SEQUENCE: 8

Asn Leu Ala Ser Ser Asn Tyr Phe Pro Thr
1               5                   10

<210> SEQ ID NO 9
<211> LENGTH: 10
<212> TYPE: PRT
<213> ORGANISM: Human papillomavirus type 16

```
<400> SEQUENCE: 9

Thr Leu Thr Ala Asp Val Met Thr Tyr Ile
1               5                   10

<210> SEQ ID NO 10
<211> LENGTH: 10
<212> TYPE: PRT
<213> ORGANISM: Human papillomavirus type 16

<400> SEQUENCE: 10

Tyr Leu Pro Pro Val Pro Val Ser Lys Val
1               5                   10

<210> SEQ ID NO 11
<211> LENGTH: 9
<212> TYPE: PRT
<213> ORGANISM: Human papillomavirus type 16

<400> SEQUENCE: 11

Tyr Asp Leu Gln Phe Ile Phe Gln Leu
1               5

<210> SEQ ID NO 12
<211> LENGTH: 9
<212> TYPE: PRT
<213> ORGANISM: Human papillomavirus type 16

<400> SEQUENCE: 12

Ile Cys Trp Gly Asn Gln Leu Phe Val
1               5

<210> SEQ ID NO 13
<211> LENGTH: 9
<212> TYPE: PRT
<213> ORGANISM: Human papillomavirus type 16

<400> SEQUENCE: 13

Phe Tyr Asn Pro Asp Thr Gln Arg Leu
1               5

<210> SEQ ID NO 14
<211> LENGTH: 9
<212> TYPE: PRT
<213> ORGANISM: Human papillomavirus type 16

<400> SEQUENCE: 14

Met His Gly Asp Thr Pro Thr Leu His
1               5

<210> SEQ ID NO 15
<211> LENGTH: 8
<212> TYPE: PRT
<213> ORGANISM: Human papillomavirus type 16

<400> SEQUENCE: 15

Glu Thr Thr Asp Leu Tyr Cys Tyr
1               5

<210> SEQ ID NO 16
<211> LENGTH: 10
<212> TYPE: PRT
<213> ORGANISM: Human papillomavirus type 16

<400> SEQUENCE: 16
```

Gln Ala Glu Pro Asp Arg Ala His Tyr Asn
1               5                   10

<210> SEQ ID NO 17
<211> LENGTH: 9
<212> TYPE: PRT
<213> ORGANISM: Human papillomavirus type 16

<400> SEQUENCE: 17

Ser Met Val Thr Ser Asp Ala Gln Ile
1               5

<210> SEQ ID NO 18
<211> LENGTH: 9
<212> TYPE: PRT
<213> ORGANISM: Human papillomavirus type 16

<400> SEQUENCE: 18

Gly Ile Leu Gly Phe Val Phe Thr Leu
1               5

<210> SEQ ID NO 19
<211> LENGTH: 10
<212> TYPE: PRT
<213> ORGANISM: Human papillomavirus type 16

<400> SEQUENCE: 19

Tyr Met Leu Asp Leu Gln Pro Glu Thr Thr
1               5                   10

<210> SEQ ID NO 20
<211> LENGTH: 9
<212> TYPE: PRT
<213> ORGANISM: Human papillomavirus type 16

<400> SEQUENCE: 20

Ser Met Asp Tyr Lys Gln Thr Gln Leu
1               5

<210> SEQ ID NO 21
<211> LENGTH: 9
<212> TYPE: PRT
<213> ORGANISM: Human papillomavirus type 16

<400> SEQUENCE: 21

Thr Leu Glu Asp Thr Tyr Arg Phe Val
1               5

<210> SEQ ID NO 22
<211> LENGTH: 9
<212> TYPE: PRT
<213> ORGANISM: Human papillomavirus type 16

<400> SEQUENCE: 22

Phe Gln Leu Cys Lys Ile Thr Leu Thr
1               5

<210> SEQ ID NO 23
<211> LENGTH: 9
<212> TYPE: PRT
<213> ORGANISM: Human papillomavirus type 16

<400> SEQUENCE: 23

Lys Val Val Ser Thr Asp Glu Tyr Val
1               5

```
<210> SEQ ID NO 24
<211> LENGTH: 9
<212> TYPE: PRT
<213> ORGANISM: Human papillomavirus type 16

<400> SEQUENCE: 24

Gln Leu Phe Val Thr Val Val Asp Thr
  1               5

<210> SEQ ID NO 25
<211> LENGTH: 9
<212> TYPE: PRT
<213> ORGANISM: Human papillomavirus type 16

<400> SEQUENCE: 25

Gly Leu Gln Tyr Arg Val Phe Arg Ile
  1               5

<210> SEQ ID NO 26
<211> LENGTH: 20
<212> TYPE: PRT
<213> ORGANISM: Human papillomavirus type 16

<400> SEQUENCE: 26

Met Ser Leu Tyr Leu Pro Ser Glu Ala Thr Val Tyr Leu Pro Pro Val
  1               5                  10                  15

Pro Val Ser Lys
             20

<210> SEQ ID NO 27
<211> LENGTH: 20
<212> TYPE: PRT
<213> ORGANISM: Human papillomavirus type 16

<400> SEQUENCE: 27

Tyr Leu Pro Pro Val Pro Val Ser Lys Val Val Ser Thr Asp Glu Tyr
  1               5                  10                  15

Val Ala Arg Thr
             20

<210> SEQ ID NO 28
<211> LENGTH: 20
<212> TYPE: PRT
<213> ORGANISM: Human papillomavirus type 16

<400> SEQUENCE: 28

Ser Thr Asp Glu Tyr Val Ala Arg Thr Asn Ile Tyr Tyr His Ala Gly
  1               5                  10                  15

Thr Ser Arg Leu
             20

<210> SEQ ID NO 29
<211> LENGTH: 20
<212> TYPE: PRT
<213> ORGANISM: Human papillomavirus type 16

<400> SEQUENCE: 29

Tyr Tyr His Ala Gly Thr Ser Arg Leu Leu Ala Val Gly His Pro Tyr
  1               5                  10                  15

Phe Pro Ile Lys
             20
```

-continued

```
<210> SEQ ID NO 30
<211> LENGTH: 20
<212> TYPE: PRT
<213> ORGANISM: Human papillomavirus type 16

<400> SEQUENCE: 30

Val Gly His Pro Tyr Phe Pro Ile Lys Lys Pro Asn Asn Lys Ile
 1               5                  10                  15

Leu Val Pro Lys
            20

<210> SEQ ID NO 31
<211> LENGTH: 20
<212> TYPE: PRT
<213> ORGANISM: Human papillomavirus type 16

<400> SEQUENCE: 31

Asn Asn Lys Ile Leu Val Pro Lys Val Ser Gly Leu Gln Tyr Arg
 1               5                  10                  15

Val Phe Arg Ile
            20

<210> SEQ ID NO 32
<211> LENGTH: 20
<212> TYPE: PRT
<213> ORGANISM: Human papillomavirus type 16

<400> SEQUENCE: 32

Gly Leu Gln Tyr Arg Val Phe Arg Ile His Leu Pro Asp Pro Asn Lys
 1               5                  10                  15

Phe Gly Phe Pro
            20

<210> SEQ ID NO 33
<211> LENGTH: 20
<212> TYPE: PRT
<213> ORGANISM: Human papillomavirus type 16

<400> SEQUENCE: 33

Pro Asp Pro Asn Lys Phe Gly Phe Pro Asp Thr Ser Phe Tyr Asn Pro
 1               5                  10                  15

Asp Thr Gln Arg
            20

<210> SEQ ID NO 34
<211> LENGTH: 20
<212> TYPE: PRT
<213> ORGANISM: Human papillomavirus type 16

<400> SEQUENCE: 34

Ser Phe Tyr Asn Pro Asp Thr Gln Arg Leu Val Trp Ala Cys Val Gly
 1               5                  10                  15

Val Glu Val Gly
            20

<210> SEQ ID NO 35
<211> LENGTH: 20
<212> TYPE: PRT
<213> ORGANISM: Human papillomavirus type 16

<400> SEQUENCE: 35

Trp Ala Cys Val Gly Val Glu Val Gly Arg Gly Gln Pro Leu Gly Val
```

```
                1               5              10              15

Gly Ile Ser Gly
        20

<210> SEQ ID NO 36
<211> LENGTH: 20
<212> TYPE: PRT
<213> ORGANISM: Human papillomavirus type 16

<400> SEQUENCE: 36

Gln Pro Leu Gly Val Gly Ile Ser Gly His Pro Leu Leu Asn Lys Leu
  1               5              10              15

Asp Asp Thr Glu
        20

<210> SEQ ID NO 37
<211> LENGTH: 20
<212> TYPE: PRT
<213> ORGANISM: Human papillomavirus type 16

<400> SEQUENCE: 37

Leu Leu Asn Lys Leu Asp Asp Thr Glu Asn Ala Ser Ala Tyr Ala Ala
  1               5              10              15

Asn Ala Gly Val
        20

<210> SEQ ID NO 38
<211> LENGTH: 20
<212> TYPE: PRT
<213> ORGANISM: Human papillomavirus type 16

<400> SEQUENCE: 38

Ser Ala Tyr Ala Ala Asn Ala Gly Val Asp Asn Arg Glu Cys Ile Ser
  1               5              10              15

Met Asp Tyr Lys
        20

<210> SEQ ID NO 39
<211> LENGTH: 20
<212> TYPE: PRT
<213> ORGANISM: Human papillomavirus type 16

<400> SEQUENCE: 39

Arg Glu Cys Ile Ser Met Asp Tyr Lys Gln Thr Gln Leu Cys Leu Ile
  1               5              10              15

Gly Cys Lys Pro
        20

<210> SEQ ID NO 40
<211> LENGTH: 20
<212> TYPE: PRT
<213> ORGANISM: Human papillomavirus type 16

<400> SEQUENCE: 40

Gln Leu Cys Leu Ile Gly Cys Lys Pro Pro Ile Gly Glu His Trp Gly
  1               5              10              15

Lys Gly Ser Pro
        20

<210> SEQ ID NO 41
<211> LENGTH: 20
<212> TYPE: PRT
```

-continued

<213> ORGANISM: Human papillomavirus type 16

<400> SEQUENCE: 41

Gly Glu His Trp Gly Lys Gly Ser Pro Cys Thr Asn Val Ala Val Asn
1               5                   10                  15

Pro Gly Asp Cys
            20

<210> SEQ ID NO 42
<211> LENGTH: 20
<212> TYPE: PRT
<213> ORGANISM: Human papillomavirus type 16

<400> SEQUENCE: 42

Asn Val Ala Val Asn Pro Gly Asp Cys Pro Pro Leu Glu Leu Ile Asn
1               5                   10                  15

Thr Val Ile Gln
            20

<210> SEQ ID NO 43
<211> LENGTH: 20
<212> TYPE: PRT
<213> ORGANISM: Human papillomavirus type 16

<400> SEQUENCE: 43

Leu Glu Leu Ile Asn Thr Val Ile Gln Asp Gly Asp Met Val Asp Thr
1               5                   10                  15

Gly Phe Gly Ala
            20

<210> SEQ ID NO 44
<211> LENGTH: 20
<212> TYPE: PRT
<213> ORGANISM: Human papillomavirus type 16

<400> SEQUENCE: 44

Asp Met Val Asp Thr Gly Phe Gly Ala Met Asp Phe Thr Thr Leu Gln
1               5                   10                  15

Ala Asn Lys Ser
            20

<210> SEQ ID NO 45
<211> LENGTH: 20
<212> TYPE: PRT
<213> ORGANISM: Human papillomavirus type 16

<400> SEQUENCE: 45

Phe Thr Thr Leu Gln Ala Asn Lys Ser Glu Val Pro Leu Asp Ile Cys
1               5                   10                  15

Thr Ser Ile Cys
            20

<210> SEQ ID NO 46
<211> LENGTH: 20
<212> TYPE: PRT
<213> ORGANISM: Human papillomavirus type 16

<400> SEQUENCE: 46

Pro Leu Asp Ile Cys Thr Ser Ile Cys Lys Tyr Pro Asp Tyr Ile Lys
1               5                   10                  15

Met Val Ser Glu
            20

-continued

<210> SEQ ID NO 47
<211> LENGTH: 20
<212> TYPE: PRT
<213> ORGANISM: Human papillomavirus type 16

<400> SEQUENCE: 47

Pro Asp Tyr Ile Lys Met Val Ser Glu Pro Tyr Gly Asp Ser Leu Phe
 1               5                  10                  15

Phe Tyr Leu Arg
            20

<210> SEQ ID NO 48
<211> LENGTH: 20
<212> TYPE: PRT
<213> ORGANISM: Human papillomavirus type 16

<400> SEQUENCE: 48

Gly Asp Ser Leu Phe Phe Tyr Leu Arg Arg Glu Gln Met Phe Val Arg
 1               5                  10                  15

His Leu Phe Asn
            20

<210> SEQ ID NO 49
<211> LENGTH: 20
<212> TYPE: PRT
<213> ORGANISM: Human papillomavirus type 16

<400> SEQUENCE: 49

Gln Met Phe Val Arg His Leu Phe Asn Arg Ala Gly Ala Val Gly Glu
 1               5                  10                  15

Asn Val Pro Asp
            20

<210> SEQ ID NO 50
<211> LENGTH: 20
<212> TYPE: PRT
<213> ORGANISM: Human papillomavirus type 16

<400> SEQUENCE: 50

Gly Ala Val Gly Glu Asn Val Pro Asp Asp Leu Tyr Ile Lys Gly Ser
 1               5                  10                  15

Gly Ser Thr Ala
            20

<210> SEQ ID NO 51
<211> LENGTH: 20
<212> TYPE: PRT
<213> ORGANISM: Human papillomavirus type 16

<400> SEQUENCE: 51

Tyr Ile Lys Gly Ser Gly Ser Thr Ala Asn Leu Ala Ser Ser Asn Tyr
 1               5                  10                  15

Phe Pro Thr Pro
            20

<210> SEQ ID NO 52
<211> LENGTH: 20
<212> TYPE: PRT
<213> ORGANISM: Human papillomavirus type 16

<400> SEQUENCE: 52

-continued

Ala Ser Ser Asn Tyr Phe Pro Thr Pro Ser Gly Ser Met Val Thr Ser
1               5                   10                  15

Asp Ala Gln Ile
            20

<210> SEQ ID NO 53
<211> LENGTH: 20
<212> TYPE: PRT
<213> ORGANISM: Human papillomavirus type 16

<400> SEQUENCE: 53

Ser Met Val Thr Ser Asp Ala Gln Ile Phe Asn Lys Pro Tyr Trp Leu
1               5                   10                  15

Gln Arg Ala Gln
            20

<210> SEQ ID NO 54
<211> LENGTH: 20
<212> TYPE: PRT
<213> ORGANISM: Human papillomavirus type 16

<400> SEQUENCE: 54

Lys Pro Tyr Trp Leu Gln Arg Ala Gln Gly His Asn Asn Gly Ile Cys
1               5                   10                  15

Trp Gly Asn Gln
            20

<210> SEQ ID NO 55
<211> LENGTH: 20
<212> TYPE: PRT
<213> ORGANISM: Human papillomavirus type 16

<400> SEQUENCE: 55

Asn Asn Gly Ile Cys Trp Gly Asn Gln Leu Phe Val Thr Val Val Asp
1               5                   10                  15

Thr Thr Arg Ser
            20

<210> SEQ ID NO 56
<211> LENGTH: 20
<212> TYPE: PRT
<213> ORGANISM: Human papillomavirus type 16

<400> SEQUENCE: 56

Val Thr Val Val Asp Thr Thr Arg Ser Thr Asn Met Ser Leu Cys Ala
1               5                   10                  15

Ala Ile Ser Thr
            20

<210> SEQ ID NO 57
<211> LENGTH: 20
<212> TYPE: PRT
<213> ORGANISM: Human papillomavirus type 16

<400> SEQUENCE: 57

Met Ser Leu Cys Ala Ala Ile Ser Thr Ser Glu Thr Thr Tyr Lys Asn
1               5                   10                  15

Thr Asn Phe Lys
            20

<210> SEQ ID NO 58
<211> LENGTH: 20

```
<212> TYPE: PRT
<213> ORGANISM: Human papillomavirus type 16

<400> SEQUENCE: 58

Thr Thr Tyr Lys Asn Thr Asn Phe Lys Glu Tyr Leu Arg His Gly Glu
 1               5                  10                  15

Glu Tyr Asp Leu
            20

<210> SEQ ID NO 59
<211> LENGTH: 20
<212> TYPE: PRT
<213> ORGANISM: Human papillomavirus type 16

<400> SEQUENCE: 59

Leu Arg His Gly Glu Glu Tyr Asp Leu Gln Phe Ile Phe Gln Leu Cys
 1               5                  10                  15

Lys Ile Thr Leu
            20

<210> SEQ ID NO 60
<211> LENGTH: 20
<212> TYPE: PRT
<213> ORGANISM: Human papillomavirus type 16

<400> SEQUENCE: 60

Ile Phe Gln Leu Cys Lys Ile Thr Leu Thr Ala Asp Val Met Thr Tyr
 1               5                  10                  15

Ile His Ser Met
            20

<210> SEQ ID NO 61
<211> LENGTH: 20
<212> TYPE: PRT
<213> ORGANISM: Human papillomavirus type 16

<400> SEQUENCE: 61

Asp Val Met Thr Tyr Ile His Ser Met Asn Ser Thr Ile Leu Glu Asp
 1               5                  10                  15

Trp Asn Phe Gly
            20

<210> SEQ ID NO 62
<211> LENGTH: 20
<212> TYPE: PRT
<213> ORGANISM: Human papillomavirus type 16

<400> SEQUENCE: 62

Thr Ile Leu Glu Asp Trp Asn Phe Gly Leu Gln Pro Pro Pro Gly Gly
 1               5                  10                  15

Thr Leu Glu Asp
            20

<210> SEQ ID NO 63
<211> LENGTH: 20
<212> TYPE: PRT
<213> ORGANISM: Human papillomavirus type 16

<400> SEQUENCE: 63

Pro Pro Pro Gly Gly Thr Leu Glu Asp Thr Tyr Arg Phe Val Thr Ser
 1               5                  10                  15

Gln Ala Ile Ala
```

-continued

20

<210> SEQ ID NO 64
<211> LENGTH: 20
<212> TYPE: PRT
<213> ORGANISM: Human papillomavirus type 16

<400> SEQUENCE: 64

Arg Phe Val Thr Ser Gln Ala Ile Ala Cys Gln Lys His Thr Pro Pro
1               5                    10                 15

Ala Pro Lys Glu
        20

<210> SEQ ID NO 65
<211> LENGTH: 20
<212> TYPE: PRT
<213> ORGANISM: Human papillomavirus type 16

<400> SEQUENCE: 65

Lys His Thr Pro Pro Ala Pro Lys Glu Asp Pro Leu Lys Lys Tyr Thr
1               5                    10                 15

Phe Trp Glu Val
        20

<210> SEQ ID NO 66
<211> LENGTH: 20
<212> TYPE: PRT
<213> ORGANISM: Human papillomavirus type 16

<400> SEQUENCE: 66

Leu Lys Lys Tyr Thr Phe Trp Glu Val Asn Leu Lys Glu Lys Phe Ser
1               5                    10                 15

Ala Asp Leu Asp
        20

<210> SEQ ID NO 67
<211> LENGTH: 20
<212> TYPE: PRT
<213> ORGANISM: Human papillomavirus type 16

<400> SEQUENCE: 67

Lys Glu Lys Phe Ser Ala Asp Leu Asp Gln Phe Pro Leu Gly Arg Lys
1               5                    10                 15

Phe Leu Leu Gln
        20

<210> SEQ ID NO 68
<211> LENGTH: 20
<212> TYPE: PRT
<213> ORGANISM: Human papillomavirus type 16

<400> SEQUENCE: 68

Pro Leu Gly Arg Lys Phe Leu Leu Gln Ala Gly Met His Gly Asp Thr
1               5                    10                 15

Pro Thr Leu His
        20

<210> SEQ ID NO 69
<211> LENGTH: 20
<212> TYPE: PRT
<213> ORGANISM: Human papillomavirus type 16

<400> SEQUENCE: 69

```
Met His Gly Asp Thr Pro Thr Leu His Glu Tyr Met Leu Asp Leu Gln
 1               5                  10                  15

Pro Glu Thr Thr
            20

<210> SEQ ID NO 70
<211> LENGTH: 20
<212> TYPE: PRT
<213> ORGANISM: Human papillomavirus type 16

<400> SEQUENCE: 70

Met Leu Asp Leu Gln Pro Glu Thr Thr Asp Leu Tyr Cys Tyr Glu Gln
 1               5                  10                  15

Leu Asn Asp Ser
            20

<210> SEQ ID NO 71
<211> LENGTH: 20
<212> TYPE: PRT
<213> ORGANISM: Human papillomavirus type 16

<400> SEQUENCE: 71

Tyr Cys Tyr Glu Gln Leu Asn Asp Ser Ser Glu Glu Glu Asp Glu Ile
 1               5                  10                  15

Asp Gly Pro Ala
            20

<210> SEQ ID NO 72
<211> LENGTH: 20
<212> TYPE: PRT
<213> ORGANISM: Human papillomavirus type 16

<400> SEQUENCE: 72

Glu Glu Asp Glu Ile Asp Gly Pro Ala Gly Gln Ala Glu Pro Asp Arg
 1               5                  10                  15

Ala His Tyr Asn
            20

<210> SEQ ID NO 73
<211> LENGTH: 20
<212> TYPE: PRT
<213> ORGANISM: Human papillomavirus type 16

<400> SEQUENCE: 73

Ala Glu Pro Asp Arg Ala His Tyr Asn Ile Val Thr Phe Cys Cys Lys
 1               5                  10                  15

Cys Asp Ser Thr
            20

<210> SEQ ID NO 74
<211> LENGTH: 20
<212> TYPE: PRT
<213> ORGANISM: Human papillomavirus type 16

<400> SEQUENCE: 74

Thr Phe Cys Cys Lys Cys Asp Ser Thr Leu Arg Leu Cys Val Gln Ser
 1               5                  10                  15

Thr His Val Asp
            20

<210> SEQ ID NO 75
```

```
<211> LENGTH: 20
<212> TYPE: PRT
<213> ORGANISM: Human papillomavirus type 16

<400> SEQUENCE: 75

Leu Cys Val Gln Ser Thr His Val Asp Ile Arg Thr Leu Glu Asp Leu
 1               5                  10                  15

Leu Met Gly Thr
            20

<210> SEQ ID NO 76
<211> LENGTH: 21
<212> TYPE: PRT
<213> ORGANISM: Human papillomavirus type 16

<400> SEQUENCE: 76

Thr Leu Glu Asp Leu Leu Met Gly Thr Leu Gly Ile Val Cys Pro Ile
 1               5                  10                  15

Cys Ser Gln Lys Pro
            20

<210> SEQ ID NO 77
<211> LENGTH: 20
<212> TYPE: PRT
<213> ORGANISM: Influenza virus type A

<400> SEQUENCE: 77

Lys Glu Tyr Leu Arg His Gly Glu Glu Gly Ile Leu Gly Phe Val Phe
 1               5                  10                  15

Thr Leu Cys Lys
            20
```